United States Patent [19]

Kutsuma et al.

[11] Patent Number: 4,672,068
[45] Date of Patent: Jun. 9, 1987

[54] ANTIHYPERTENSIVE 1,4-DIHYDROPYRIDINES HAVING A CONJUGATED ESTER

[75] Inventors: Teruo Kutsuma; Hiroshi Ikawa; Yoshiaki Sato, all of Tokyo, Japan

[73] Assignee: Fujirebio Kabushiki Kaisha, Tokyo, Japan

[21] Appl. No.: 727,692

[22] Filed: Apr. 26, 1985

[30] Foreign Application Priority Data

May 4, 1984 [JP] Japan ................................. 59-88411
Jun. 20, 1984 [JP] Japan ............................... 59-125379

[51] Int. Cl.$^4$ ................. C07D 211/90; C07D 401/12; C07D 405/12; A61K 31/455
[52] U.S. Cl. ................................. 514/336; 514/343; 514/356; 546/281; 546/283; 546/284; 546/321
[58] Field of Search ............... 546/321, 281, 283, 284; 514/336, 343, 356

[56] References Cited

U.S. PATENT DOCUMENTS

| | | | |
|---|---|---|---|
| 4,044,141 | 8/1977 | Bossert et al. | 546/321 |
| 4,370,334 | 1/1983 | Sato | 546/321 |
| 4,532,248 | 7/1985 | Franckowiak et al. | 514/89 |

FOREIGN PATENT DOCUMENTS

0088276 9/1983 European Pat. Off. ............ 546/321
51-108075 9/1976 Japan .

OTHER PUBLICATIONS

Derwent Abstract of Belgian No. 893,984, 1/31/83.

Bossert, F. et al, "4-Aryldihydropyridines" Angew. Chem. Int. Ed. Engl., 20 (1981) pp. 762-769.

Schramm, M. et al, "Novel Dihydropyridines with Positive Inotropic Action" Nature, vol. 303 (9 Jun. '83), pp. 535-537.

*Primary Examiner*—John M. Ford
*Assistant Examiner*—Dale A. Bjorkman
*Attorney, Agent, or Firm*—Flynn, Thiel, Boutell & Tanis

[57] ABSTRACT

1,4-dihydropyridine derivatives represented by the following general formula,

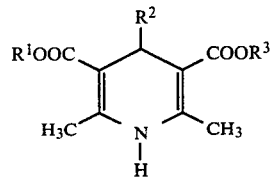

in which $R^3$ is a combination of an unsaturated straight chain hydrocarbon group or derivative thereof connected by a single bond with an unsaturated hydrocarbon group or derivative thereof so that the unsaturated carbon atoms of the two groups are in conjugated relationship. These compounds have a hypotensive action the effective time of which is long, which makes the blood pressure descend slowly, and the toxicity of which is low.

19 Claims, 1 Drawing Figure

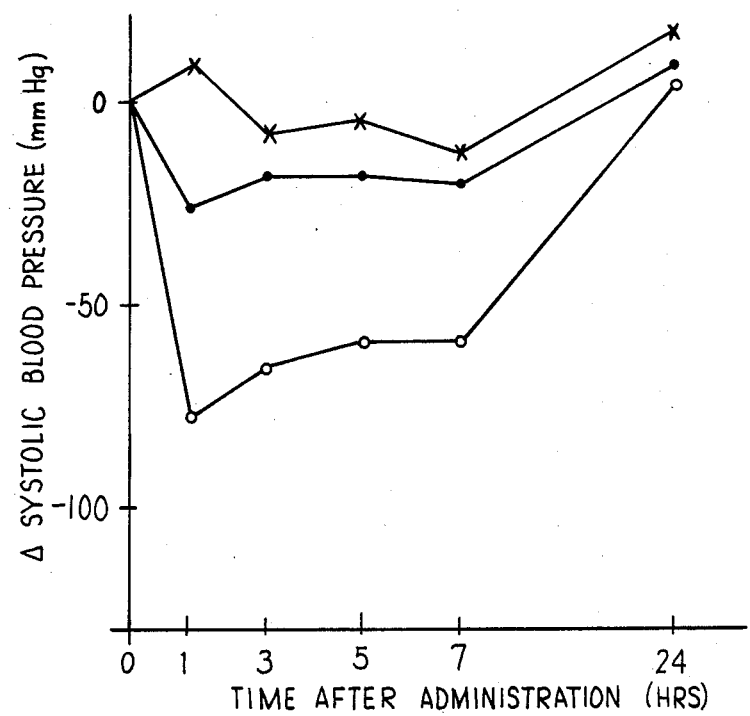

ANTIHYPERTENSIVE 1,4-DIHYDROPYRIDINES HAVING A CONJUGATED ESTER

This invention relates to 1,4-dihydropyridine derivatives having hypotensive activity.

It has been known that some 1,4-dihydropyridine derivatives have hypotensive activity. For example, 4-(o-nitrophenyl)-2,6-dimethyl-1,4-dihydropyridine-3,5-dicarboxylic acid dimethyl ester (U.S. Pat. No. 3,644,627; hereinafter referred to as "nifedipine") and 4-(m-nitrophenyl)-2,6-dimethyl-1,4-dihydropyridine-3,5-dicarboxylic acid-3-methyl ester-5-[2-(benzylmethylamino)-ethyl]ester hydrochloride (Japanese Patent Publication No. 45075/1980; hereinafter referred to as "nicardipine") have already been utilized as medicines having hypotensive activity and coronary vasodilation activity. Moreover, it is also known that many compounds similar to nifedipine and nicardipine and represented by the following general formula (I) also have hypotensive activity (Japanese Patent Publication No. 29989/1980, ibid No. 29990/1980, Japanese Patent Application Kokai No. 64571/1980, etc.)

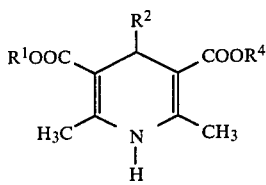

(I)

in which $R^1$ is methyl group, ethyl group, etc., $R^2$ is 3-nitrophenyl group, etc., and $R^4$ is ethyl group, isopropyl group, allyl group, propargyl group, etc.

However, these compounds have the disadvantage that their duration (time) of activity is short. For example, it has been reported that when 10 μg/kg of nicardipine, the duration (time) of activity of which is longer than that of nifedipine, was injected into a vein of a dog, the duration of activity was only about 30 to 40 minutes (Arzneim-Forsch, Vol. 22, p 33 (1976), ibid., Vol. 26, p 2172 (1982), Tohoigakkai Zasshi, Vol. 26, No. 2, p 48 (1972).

Generally, it is preferred that medicines for treating hypertension have a long duration of activity and they should make the blood pressure descend slowly.

It is an object of the invention to provide compounds having hypotensive activity, which exhibit such activity for a long time after administration and which make the blood pressure descend slowly.

It is another object of the invention to provide compounds having hypotensive activity which have a low toxicity and which do not exhibit significant side effects.

These and other objects of the invention will be apparent from the following description.

The 1,4-dihydropyridine derivatives of the invention are characterized by the replacement of $R^4$ in the compounds of formula (I), such as ethyl group, isopropyl group, allyl group, propargyl group, etc., by a univalent group which is a combination of an unsaturated straight chain hydrocarbon or derivative thereof, as a first moiety, joined by a univalent bond with an unsaturated hydrocarbon, organic unsaturated heterocyclic ring or derivatives thereof, as a second moiety.

Thus, the 1,4-dihydropyridine derivatives of the invention are represented by the following general formula,

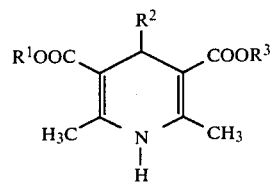

(II)

in which $R^1$ represents a saturated or unsaturated, straight chain, branched chain or cyclic, hydrocarbon group having a carbon atom number of from 1 to 6 or a derivative thereof in which one or more carbon atoms are replaced by oxygen atom(s) or sulfur atom(s) and/or in which one or more hydrogen atoms are substituted by halogen atom(s), cyano groups, aryl group(s), heteroaromatic group(s), aryloxy group(s), arylthio group(s), or amino group(s), $R^2$ represents an aryl group, a heteroaromatic group or derivatives thereof in which one or more hydrogen atoms are substituted by alkyl group(s), alkoxy group(s), halogen atom(s), alkylthio group(s), trihalomethyl group(s), nitro group(s) or cyano group(s), and $R^3$ represents a group $-R^5-R^6$, in which $R^5$ is an unsaturated straight chain hydrocarbon group or derivative thereof in which one or more hydrogen atoms are substituted by alkyl group(s), aralkyl group(s), aryl group(s), and $R^6$ is an unsaturated hydrocarbon group, an organic unsaturated heterocyclic group or derivative thereof, wherein the unsaturated carbon bond of $R^6$ is connected to the unsaturated carbon bond of the above unsaturated straight chain hydrocarbon $R^5$ or its derivative by a single bond. When both of $R^5$ and $R^6$ are ethylenically unsaturated, the group $-R^5R^6$ has a molecular fragment of the formula

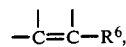

wherein the double bond of $R^6$ is conjugated with the olefinic linkage of $R^5$. For example, when $R^6$ is an unsaturated ring, then that unsaturated ring is conjugated with the olefinic linkage of $R^5$, for example,

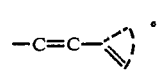

When $R^6$ is an unsaturated aliphatic hydrocarbon, then there is provided a conjugated diene structure, for example,

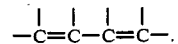

The same type of analysis applies when $R^5$ and/or $R^6$ contain a triple bond.

The hydrocarbon group of $R^1$ can be saturated or unsaturated, and it can be straight chain, branched chain or cyclic. The carbon number of the hydrocarbon group $R^1$ is usually 1 to 6. Such a hydrocarbon group includes methyl, ethyl, n-propyl, isopropyl, n-butyl, isobutyl, tert-butyl, n-pentyl, n-hexyl, allyl, 3-butenyl, crotyl, 3-butene-2-yl, 2-butynyl, 3-butynyl, cyclohexyl, 2-pentyl, 3-pentyl, 4-penten-1-yl, 3-penten-2-yl, 2-penten-1-yl, 2,4-hexadienyl, 2-hexen-1-yl, 1-hexen-3-yl, propargyl, cyclopropylmethyl, 3-pentynyl, 2-hexen-3-yl-1-yl and 2-cyclohexenyl groups. One or more carbon atoms of the skeleton of the hydrocarbon group $R^1$ can be replaced by oxygen atom(s) or sulfur atom(s). Such derivatives of the hydrocarbon group $R^1$ include 2-methoxyethyl, 2-ethoxyethyl, 2-(2-methoxyethoxy)ethyl, 2-butoxyethyl, 2-(2-ethoxyethoxy)ethyl, 3-methoxybutyl, 4-methoxy-3-butene-2-yl, 2-(2-butoxyethoxy)ethyl, 2-cyclohexyloxyethyl, 2-methylthioethyl, 2-ethylthioethyl, 3-methylthiobutyl and 2-cyclohexylthioethyl groups. One or more hydrogen atoms of the hydrocarbon group $R^1$ or its derivatives mentioned above can be substituted by halogen atom(s), cyano group(s), aryl group(s), aryloxy group(s), arylthio group(s), heteroaromatic group(s) or amino group(s). The halogen atom includes chlorine atom, bromine atom and fluorine atom. The aryl group includes phenyl, naphthyl, nitrophenyl, chlorophenyl, dichlorophenyl, cyanophenyl, fluorophenyl, methoxyphenyl, methylthiophenyl, α,α,α-trifluorotolyl, tolyl, biphenyl, methylsulfonylphenyl, methylsulfinylphenyl and azidophenyl groups. The heteroaromatic group includes thienyl, furyl, pyrazolyl, imidazolyl, oxazolyl, isoxazolyl, thiazolyl, pyridyl, pyridazinyl, pyrimidinyl, pyrazinyl, quinolyl, isoquinolyl, indolyl, benzimidazolyl, quinazolyl and quinoxalyl. The aryloxy group includes phenoxy, naphthoxy, aminophenoxy, nitrophenoxy, chlorophenoxy, cyanophenoxy and methoxyphenoxy groups. The heteroaromatic group includes benzimidazolyloxy, indolyloxy, isoquinolyloxy, pyridylthio, 4-methylquinolyloxy and pyrimidinyloxy. The arylthio group includes phenylthio. The heteroaromatic group includes benzimidazolylthio, benzthiazolylthio, benzoxazolylthio, imidazolylthio, pyrimidinylthio and pyridylthio groups. The amino group includes dimethylamino, diethylamino, benzylmethylamino, piperidino, 1-pyrrolidinyl, morpholino, anilino, methylamino, ethylamino, di-n-propylamino and benzylamino groups.

$R^2$ is an aryl group, a heteroaromatic group or derivatives thereof. The aryl groups include phenyl, and naphthyl groups. The heteroaromatic groups include thienyl, furyl, pyrazolyl, imidazolyl, oxazolyl, isoxazolyl, thiazolyl, pyridyl, pyridazinyl, pyrimidinyl, pyrazinyl, quinolyl, isoquinolyl, indolyl, benzimidazolyl, quinazolyl and quinoxalyl. One or more hydrogen atoms of the aryl group or the heteroaromatic group can be substituted by alkyl groups(s), alkoxy groups(s), halogen atom(s), alkylthio group(s), trihalomethyl group(s), nitro group(s) and cyano group(s). The alkyl group includes methyl, ethyl, n-propyl, i-propyl, n-butyl, i-butyl, t-butyl, cyclohexyl and cyclopropyl groups, the alkoxy group includes methoxy, ethoxy, n-propoxy, i-propoxy, and t-butoxy groups, and the alkylthio group includes methylthio, ethylthio, n-propylthio, i-propylthio and t-butylthio groups. The halogen atom includes chlorine atom, bromine atom, iodine atom and fluorine atom. Examples of the trihalomethyl are trichloromethyl and trifluoromethyl groups.

$R^3$ is a $-R^5R^6$ group which is a combination of an unsaturated straight chain hydrocarbon moiety or derivative thereof ($R^5$) with an unsaturated moiety, an organic unsaturated heterocyclic group or derivative thereof ($R^6$). One or more hydrogen atoms of $R^5$ can be substituted by alkyl group(s) such as methyl, ethyl, n-propyl, i-propyl, n-butyl, t-butyl and cyclohexyl groups, aralkyl group(s) such as benzyl group or aryl group(s) such as phenyl, naphthyl, nitrophenyl, chlorophenyl, dichlorophenyl, cyanophenyl, fluorophenyl, methoxyphenyl, methylthiophenyl, α,α,α-trifluorotolyl, tolyl, biphenyl, methylsulfonylphenyl, methylsulfinylphenyl and azidophenyl groups, or organic unsaturated heterocyclic group(s) such as thienyl, furyl, pyrazolyl, imidazolyl, oxazolyl, isoxazolyl, thiazolyl, pyridyl, pyridazinyl, pyrimidinyl, pyrazinyl, quinolyl, isoquinolyl, indolyl, benzimidazolyl, quinazolyl and quinoxalyl.

The unsaturated moiety $R^6$ can be a straight chain hydrocarbon. The moiety $R^6$ can also be an aryl group, a heteroaromatic group or derivatives thereof, the same as defined above for $R^2$.

The unsaturated carbon atom of the above moiety $R^6$ is connected to the unsaturated carbon atom of the above unsaturated straight chain hydrocarbon moiety $R^5$ or its derivative by a single bond. As a result, the unsaturated carbon atoms are conjugated.

Among the 1,4-dihydropyridine derivatives which are exemplified hereinafter, the derivatives of Example 1 are the most preferable, and the derivatives of Example 55 are the second most preferable in a synthetic evaluation.

Geometrical isomers of the 1,4-dihydropyridine derivatives are usually present.

The 1,4-dihydropyridine derivatives, according to the invention, have hypotensive activity. When 1 mg/kg of any one of the derivatives, according to the invention, suspended in gum arabic solution in a concentration of 5%, is injected into the instinum duodenum of a rat of more than 10 weeks age and having spontaneous hypertension, there occurs reduction of the blood pressure of the rat in an amount of more than about 20 mmHg, usually more than about 35 mmHg. The time, after administration, until the lowest blood pressure is reached is more than 20 minutes, usually more than 40 minutes. The half-life period is more than 60 minutes, usually more than 120 minutes. Both the cis isomer and the trans isomer have hypotensive activity.

The 1,4-dihydropyridine derivatives can be produced by the following methods.

Method 1

The compound having the following general formula

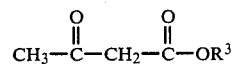

the compound having the following general formula $R^2-CHO$ and the compound having the following general formula

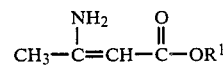

are mixed with each other without a solvent or in a solvent that is inactive to the reaction, such as methanol, ethanol, propanol, isopropanol, benzene, toluene, dioxane, tetrahydrofuran, dimethyl sulfoxide and dimethylformamide, and heated to produce the derivative of the invention. The preferable reaction temperature is 50° to 150° C., and the reaction time is usually 0.5 to 15 hours.

Method 2

Using the compound having the following general formula

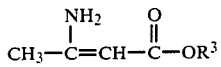

the compound having the following general formula

and the compound having the following general formula

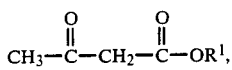

the derivative of the invention can be produced in the same manner as described in the method 1.

Method 3

Using

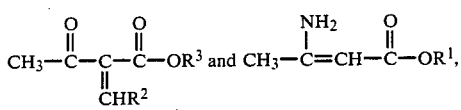

the derivative of the invention can be produced in the same manneer as described in the method 1.

Method 4

Using

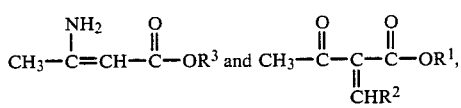

the derivative of the invention can be produced in the same manner as described in the method 1.

Method 5

Using

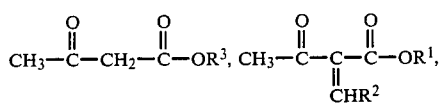

and $NH_3$, the derivative of the invention can be produced in the same manner as described in the method 1.

Method 6

Using

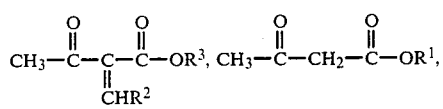

and $NH_3$, the derivative of the invention can be produced in the same manner as described in the method 1.

Method 7

The compound having the following general formula

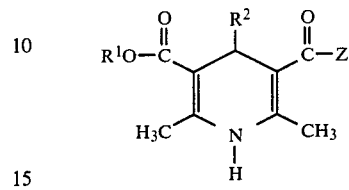

in which Z represents a hydroxyl group or an acid residue of an active ester such as a halogen atom, methylsulfonyloxy group, paratoluenesulfonyloxy group or benzotriazole-1-oxy group and an alcohol having the following formula

are allowed to react to produce the derivative of the invention. When Z is a hydroxyl group, the reaction can be carried out in the presence of an acid, such as hydrogen chloride, sulfuric acid or boron trifluoride, or a dehydrating condensing agent, such as dicyclohexylcarbodiimide, in an inactive solvent. A base, such as 4-dimethylaminopyridine, can be present in the reaction mixture, if necessary. When Z is an active ester residue, the reaction can be carried out in an inert solvent, in the presence of a base, such as triethylamine, 4-dimethylaminopyridine, pyridine or potassium carbonate, if necessary.

Method 8

A compound of the formula

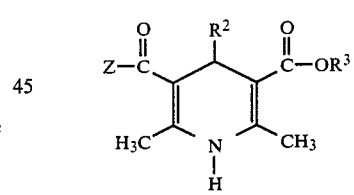

and a compound of the formula $R^1OH$ are allowed to react in the same manner as described in the method 7 to produce the derivative of the invention.

The derivatives so produced can be separated from the reaction mixture and purified according to conventional techniques.

The 1,4-dihydropyridine derivatives of the invention have strong vasodilator and hypotensive activities. The time, after administration, to reach the lowest blood pressure (maximum antihypertensive effect) is long, and the biological half-life period is sufficiently long. These derivatives are useful as a drug for treating hypertension.

BRIEF DESCRIPTION OF THE DRAWING

The drawing is a graph showing the results of the test described in Example 90.

EXAMPLE 1

3.51 g (10 mM) of 2-(3-nitrobenzylidene)acetoacetic acid cinnamyl ester was mixed with 1.38 g (12 mM) of 3-aminocrotonic acid methyl ester, and heated at 120° for 3 hours. The reaction mixture was separated by silica gel column chromatography, and 3.00 g of cinnamyl methyl 4-(3-nitrophenyl)-2,6-dimethyl-1,4-dihydropyridine-3,5-dicarboxylate (trans) was obtained (yield 67%). This derivative was recrystallized once with methanol.

Elemental Analysis; $C_{25}H_{24}N_2O_6$. Calcd. (%) C: 66.95, H: 5.39, N: 6.25. Found (%) C: 67.03, H: 5.31, N: 6.20.

(trans)

m.p.; 143.5°–144.5° C.
IR (cm$^{-1}$); $\nu_{NH}$3370, $\nu_{CO}$1700, $\nu_{NO_2}$1530, 1350.
NMR $\delta_{CDCl_3}$; 2.34(s, 6H), 3.60 (s, 3H), 4.69(d, 2H), 5.13(s, 1H), 6.14(tt, 1H), 6.55(d, 1H), 7.1–8.1(m, 9H).

(cis)

m.p.; 136°–137° C.
IR (cm$^{-1}$); $\nu_{NH}$3360, $\nu_{CO}$1700, 1650, $\nu_{NO_2}$1530 1350.
NMR $\delta_{CDCl_3}$; 2.30(s, 6H), 3.60(s, 3H), 4.80(d, 1H), 5.10s, 1H), 5.77(tt, 1H), 6.56(d, 1H), 6.64(bs, 1H), 7.1–8.1(m, 9H).

EXAMPLES 2–40

The following 1,4-dihydropyridine derivatives were prepared in the same manner as described in Example 1 by suitably changing the starting materials. When the product was oily, the recrystallization was not carried out.

Example 2

Cinnamyl methyl 4-(4-methylthiophenyl)-2,6-dimethyl-1,4-dihydropyridine-3,5-dicarboxylate Elemental Analysis; $C_{26}H_{27}NO_4S$. Calcd. (%) C: 69.46, H: 6.05, N: 3.12. Found (%) C: 69.51, H: 5.94, N: 3.07.

m.p.; 164.2°–170.8° C.
IR (cm$^{-1}$); $\nu_{NH}$ 3330, $\nu_{CO}$ 1680.
NMR $\delta_{CDCl_3}$; 2.26(s, 3H), 2.28(s, 3H), 2.35(s, 3H), 3.61(s, 3H), 4.0–4.82(m, 2H), 5.00(s, 1H), 5.87–6.69(m, 2H), 6.17(s, 1H), 6.7–7.8(m, 9H).

Example 3

Cinnamyl methyl 4-(2-cyanophenyl)-2,6-dimethyl-1,4-dihydropyridine-3,5-dicarboxylate Elemental Analysis; $C_{26}H_{24}N_2O_4$. Calcd. (%) C: 72.71, H: 5.87, N: 6.52. Found (%) C: 72.75, H: 5.79, N: 6.48.

m.p.: Oily.
IR (cm$^{-1}$); $\nu_{NH}$ 3330, $\nu_{CN}$ 2230, $\nu_{CO}$ 1700.
NMR $\delta_{CDCl_3}$; 2.32(s, 6H), 3.61(s, 3H), 4.5–4.9(m, 2H), 5.35(s, 1H), 5.9–6.3(m, 2H), 6.74(s, 1H), 6.9–7.6(m, 9H).

Example 4

4-phenyl-3-butenyl methyl 4-(3-nitrophenyl)-2,6-dimethyl-1,4-dihydropyridine-3,5-dicarboxylate Elemental Analysis; $C_{26}H_{26}N_2O_6$. Calcd. (%) C: 67.52, H: 5.67, N: 6.06. Found (%) C: 67.58, H: 5.74, N: 6.04.

m.p.: Oily.
IR (cm$^{-1}$); $\nu_{NH}$ 3330, $\nu_{CO}$ 1700, $\nu_{NO_2}$ 1530, 1350.
NMR $\delta_{CDCl_3}$; 2.30(s, 6H), 2.55(t, 2H), 3.55(s, 3H), 4.15(t, 2H), 5.10(s, 1H), 6.0–6.6(m, 2H), 6.59(s, 1H), 7.0–8.1(m, 10H).

Example 5

3-phenyl-2-butenyl methyl 4-(3-nitrophenyl)-2,6-dimethyl-1,4-dihydropyridine-3,5-dicarboxylate Elemental Analysis; $C_{26}H_{26}N_2O_6$. Calcd. (%) C: 67.52, H: 5.67, N: 6.06. Found (%) C: 67.59, H: 5.63, N: 6.01.

m.p.; Oily.
IR (cm$^{-1}$); $\nu_{NH}$ 3330, $\nu_{CO}$ 1690, $\nu_{NO_2}$ 1530, 1350.
NMR $\delta_{CDCl_3}$; 2.00(s, 3H), 3.31(s, 6H), 3.53(s, 3H), 4.62(d, 2H), 5.04(s, 1H), 6.03(t, 1H), 6.25(brs, 1H), 7.1–8.1(m, 9H).

Example 6

1-tert-butyl-3-phenyl-2-propenyl methyl 4-(3-nitrophenyl)-2,6-dimethyl-1,4-dihydropyridine-3,5-dicarboxylate Elemental Analysis; $C_{29}H_{32}N_2O_6$. Calcd. (%) C: 69.03, H: 6.39, N: 5.55. Found (%) C: 69.06, H: 6.43, N: 5.51.

m.p.; 166.5°–168° C.
IR (cm$^{-1}$); $\nu_{NH}$ 3340, $\nu_{CO}$ 1700, 1670 $\nu_{NO_2}$ 1530, 1350.
NMR $\delta_{CDCl_3}$; 1.00(s, 9H), 2.34(s, 6H), 3.64(s, 3H), 5.10(m, 1H), 5.18(s, 1H), 5.9–6.6(m, 3H), 7.1–8.2(m, 9H).

Example 7

3-(2furyl)-2-propenyl methyl 4-(3-nitrophenyl)-2,6-dimethyl-1,4-dihydropyridine-3,5-dicarboxylate Elemental Analysis; $C_{23}H_{22}N_2O_7$. Calcd. (%) C: 63.01, H: 5.06, N: 6.39. Found (%) C: 63.05, H: 5.01, N: 6.36.

m.p.; 157°–159.5° C.
IR (cm$^{-1}$); $\nu_{NH}$ 3320, $\nu_{CO}$ 1705, 1655 $\nu_{NO_2}$ 1530, 1350.
NMR $\delta_{CDCl_3}$; 2.34(s, 6H), 3.62(s, 3H), 4.64(d, 2H), 5.12(s, 1H), 6.20(m, 5H), 7.1–8.1(m, 5H).

Example 8

1-isopropyl-3-phenyl-2-propenyl methyl 4-(3-nitrophenyl)-2,6-dimethyl-1,4-dihydropyridine-3,5-dicarboxylate Elemental Analysis; $C_{28}H_{30}N_2O_6$.
Calcd. (%) C: 68.56, H: 6.16, N: 5.71. Found (%) C: 68.58, H: 6.13, N: 5.69.

m.p.; Oily.
IR (cm$^{-1}$); $\nu_{NH}$ 3320, $\nu_{CO}$ 1680, $\nu_{NO_2}$ 1530, 1350.
NMR $\delta_{CDCl_3}$; 1.00(d, 6H), 2.36(s, 6H), 3.64(s, 3H), 5.16(s, 1H), 5.18(m, 1H), 5.9–6.8(m, 3H), 7.0–8.2(m, 9H).

Example 9

3,3-diphenyl-2-propenyl methyl 4-(3-nitrophenyl)-2,6-dimethyl-1,4-dihydropyridine-3,5-dicarboxylate Elemental Analysis; $C_{31}H_{28}N_2O_6$. Calcd. (%) C: 70.97, H: 5.38, N: 5.34. Found (%) C: 71.04, H: 5.32, N: 5.28.

m.p.; Oily.

IR (cm$^{-1}$); $\nu_{NH}$ 3330, $\nu_{CO}$ 1705, $\nu_{NO_2}$ 1530, 1350.

NMR $\delta_{CDCl_3}$; 2.30(s, 6H), 3.61(s, 3H), 4.57(d, 2H), 5.10(s, 1H), 5.90(d, 1H), 6.18(s, 1H), 6.9–8.05(m, 14H).

Example 10

1-propyl-3-phenyl-2-propenyl methyl 4-(3-nitrophenyl)-2,6-dimethyl-1,4-dihydropyridine-3,5-dicarboxylate Elemental Analysis; $C_{28}H_{30}N_2O_6$. Calcd. (%) C: 68.56, H: 6.16, N: 5.71. Found (%) C: 68.61, H: 6.12, N: 5.68.

m.p.; Oily.

IR (cm$^{-1}$); $\nu_{NH}$ 3330, $\nu_{CO}$ 1680, $\nu_{NO_2}$ 1530, 1350.

NMR $\delta_{CDCl_3}$; 0.7–2.0(m, 7H), 2.32(s, 6H), 3.60(s, 3H), 5.10(s, 1H), 5.35 (m, 1H), 5.9–6.8(m, 3H), 7.1–8.2(m, 9H).

Example 11

4-α-thienyl-3-butenyl methyl 4-(3-nitrophenyl)-2,6-dimethyl-1,4-dihydropyridine-3,5-dicarboxylate Elemental Analysis; $C_{24}H_{24}N_2O_6S$. Calcd. (%) C: 61.53, H: 5.16, N: 5.98. Found (%) C: 61.57, H: 5.13, N: 5.79.

m.p.; Oily.

IR (cm$^{-1}$); $\nu_{NH}$ 3330, $\nu_{CO}$ 1690, $\nu_{NO_2}$ 1530, 1350.

NMR $\delta_{CDCl_3}$; 2.33(s, 6H), 2.52(t, 2H), 3.58(s, 3H), 4.16(t, 3H), 5.11(s, 1H), 5.5–8.2(m, 10H).

Example 12

4-β-naphthyl-3-butenyl methyl 4-(3-nitrophenyl)-2,6-dimethyl-1,4-dihydropyridine-3,5-dicarboxylate Elemental Analysis; $C_{30}H_{28}N_2O_6$. Calcd. (%) C: 70.30, H: 5.51, N: 5.47. Found (%) C: 70.34, H: 5.47, N: 5.42.

(trans)

m.p.; 180.5°–181.5° C.

IR (cm$^{-1}$); $\nu_{NH}$ 3370, $\nu_{CO}$ 1700, 1660, $\nu_{NO_2}$ 1535, 1355.

NMR $\delta_{CDCl_3}$; 2.26(s, 6H), 2.52(m, 2H), 3.52(s, 3H), 4.20(t, 2H), 5.10(s, 1H), 6.10(tt, 1H), 6.25(bs, 1H), 6.54(d, 1H), 7.0–8.1(m, 11H).

(cis)

m.p.; 139°–140° C.

IR (cm$^{-1}$); $\nu_{NH}$ 3360, $\nu_{CO}$ 1710, 1650, $\nu_{NO_2}$ 1530, 1350.

NMR $\delta_{CDCl_3}$; 2.28(s, 6H), 2.75(m, 2H), 3.56(s, 3H), 4.14(t, 2H), 5.05(s, 1H), 5.60(tt, 1H), 6.25(bs, 1H), 6.60(d, 1H), 7.1–8.2(m, 11H).

Example 13

Cinnamyl 2-methoxyethyl 4-(3-nitrophenyl)-2,6-dimethyl-1,4-dihydropyridine-3,5-dicarboxylate Elemental Analysis; $C_{27}H_{28}N_2O_7$. Calcd. (%) C: 65.84, H: 5.73, N: 5.69. Found (%) C: 65.88, H: 5.70, N: 5.66.

m.p.; 115.5°–116.5° C.

IR (cm$^{-1}$); $\nu_{NH}$ 3380, $\nu_{CO}$ 1710, 1680, $\nu_{NO_2}$ 1530, 1350.

NMR $\delta_{CDCl_3}$; 2.34(s, 6H), 3.25(s, 3H), 3.50(t, 2H), 4.15(t, 2H), 4.68(d, 2H), 5.15(s, 1H), 5.9–6.9(m, 3H), 7.1–8.2(m, 9H).

Example 14

Cinnamyl isopropyl 4-(3-nitrophenyl)-2,6-dimethyl-1,4-dihydropyridine-3,5-dicarboxylate Elemental Analysis; $C_{27}H_{28}N_2O_6$. Calcd. (%) C: 68.05, H: 5.92, N: 5.88. Found (%) C: 68.10, H: 5.86, N: 5.85.

m.p.; Oily.

IR (cm$^{-1}$); $\nu_{NH}$ 3320, $\nu_{CO}$ 1680, $\nu_{NO_2}$ 1530, 1350.

NMR $\delta_{CDCl_3}$; 1.10(d, 3H), 1.25(d, 3H), 2.32(s, 6H), 4.70(d, 2H), 4.92(m, 1H), 5.10(s, 1H), 5.9–6.8(m, 3H), 7.1–8.2(m, 9H).

Example 15

Cinnamyl ethyl 4-(3-nitrophenyl)-2,6-dimethyl-1,4-dihydropyridine-3,5-dicarboxylate Elemental Analysis; $C_{26}H_{26}N_2O_6$. Calcd. (%) C: 67.52, H: 5.67, N: 6.06. Found (%) C: 67.57, H: 5.71, N: 6.18.

m.p.; 139.5°–140.5° C.

IR (cm$^{-1}$); $\nu_{NH}$ 3380, $\nu_{CO}$ 1710, 1680, $\nu_{NO_2}$ 1530, 1350.

NMR $\delta_{CDCl_3}$; 1.20(t, 3H), 2.32(s, 6H), 4.08(q, 2H), 4.68(d, 2H), 5.18(s, 1H), 5.9–6.9(m, 3H), 7.1–8.2(m, 9H).

Example 16

5-phenyl-2,4-pentadienyl methyl 4-(3-nitrophenyl)-2,6-dimethyl-1,4-dihydropyridine-3,5-dicarboxylate Elemental Analysis; $C_{27}H_{26}N_2O_6$.

Calcd. (%) C: 68.34, H: 5.52, N: 5.90. Found (%) C: 68.45, H: 5.37, N: 5.77.

m.p.; 146° C.

IR (cm$^{-1}$); $\nu_{NH}$ 3350, $\nu_{CO}$ 1700, 1650, $\nu_{NO_2}$ 1530, 1350.

NMR $\delta_{CDCl_3}$; 2.34(s, 6H), 3.60(s, 3H), 4.62(d, 2H), 5.10(s, 1H), 5.5–6.8(m, 5H), 7.1–8.1(m, 9H).

Example 17

4-(4-cyanophenyl)-3-butenyl methyl 4-(3-nitrophenyl)-2,6-dimethyl-1,4-dihydropyridine-3,5-dicarboxylate Elemental Analysis; $C_{27}H_{25}N_3O_6$. Calcd. (%) C: 66.52, H: 5.17, N: 8.62. Found (%) C: 66.50, H: 5.19, N: 8.59.

m.p.; 161.3°–164.8° C.

IR (cm$^{-1}$); $\nu_{NH}$ 3330, $\nu_{CO}$ 1690, $\nu_{NO_2}$ 1530, 1350

NMR $\delta_{CDCl_3}$; 2.35(s, 6H), 2.58(t, 2H), 3.58(s, 3H), 4.20(t, 2H), 5.08(s, 1H), 6.15–6.40(m, 3H), 7.2–8.1(m, 8H).

Example 18

4-(4-methoxyphenyl)-3-butenyl methyl 4-(3-nitrophenyl)-2,6-dimethyl-1,4-dihydropyridine-3,5-dicarboxylate Elemental Analysis; $C_{28}H_{27}N_2O_7$. Calcd. (%) C: 66.79, H: 5.41, N: 5.56. Found (%) C: 66.81, H: 5.37, N: 5.49.

m.p.; 137°–140.5° C.

IR (cm$^{-1}$); $\nu_{NH}$ 3360, $\nu_{CO}$ 1705, 1655, $\nu_{NO_2}$ 1530, 1350.

NMR $\delta_{CDCl_3}$; 2.30(s, 6H), 2.58(m, 2H), 3.58(s, 3H), 3.76(s, 3H), 4.14(t, 2H), 5.08(s, 1H), 5.2–6.9(m, 3H), 7.1–8.1(m, 8H).

Example 19

4-(N-methyl-2-pyrrolyl)-butenyl methyl 4-(3-nitrophenyl)-2,6-dimethyl-1,4-dihydropyridine-3,5-dicarboxylate Elemental Analysis; $C_{25}H_{27}N_3O_6$. Calcd. (%) C: 64.51, H: 5.85, N: 9.03. Found (%) C: 64.58, H: 5.80, N: 8.97.

m.p.; Oily.

IR (cm$^{-1}$); $\nu_{NH}$ 3330, $\nu_{CO}$ 1690, $\nu_{NO_2}$ 1530, 1350.

NMR $\delta_{CDCl_3}$; 2.30(s, 6H), 2.60(m, 2H), 3.53(s, 3H), 3.60(s, 3H), 4.15(t, 2H), 5.06(s, 1H), 5.1–6.6(m, 6H), 7.1–8.1(m, 4H).

Example 20

4-(p-methylphenyl)-3-butenyl methyl 4-(3-nitrophenyl)-2,6-dimethyl-1,4-dihydropyridine-3,5-dicarboxylate Elemental Analysis; $C_{27}H_{28}N_2O_6$. Calcd. (%) C: 68.05, H: 5.92, N: 5.88. Found (%) C: 68.11, H: 5.83, N: 5.82.

m.p.; Oily.

IR (cm$^{-1}$); $\nu_{NH}$ 3330, $\nu_{CO}$ 1690, $\nu_{NO_2}$ 1530, 1350.

NMR $\delta_{CDCl_3}$; 2.30(s, 9H), 2.52(t, 2H), 3.55(s, 3H), 4.13(t, 2H), 5.07(s, 1H), 6.0–8.1(m, 11H).

Example 21

4(p-nitrophenyl)-3-butenyl methyl 4-(3-nitrophenyl)-2,6-dimethyl-1,4-dihydropyridine-3,5-dicarboxylate Elemental Analysis; $C_{26}H_{25}N_3O_8$. Calcd. (%) C: 61.53, H: 4.97, N: 8.28. Found (%) C: 61.59, H: 4.79, N: 8.16.

m.p.; 111°–113.5° C.

IR (cm$^{-1}$); $\nu_{NH}$ 3340, $\nu_{CO}$ 1690, 1650, $\nu_{NO_2}$ 1525, 1350.

NMR $\delta_{CDCl_3}$; 2.32(s, 6H), 2.65(m, 2H), 3.58(s, 3H), 4.15(m, 2H), 5.04(s, 1H), 5.5–6.6(m, 3H), 7.1–8.2(m, 8H).

Example 22

2-methyl-3-phenyl-2-propenyl methyl 4-(3-nitrophenyl)-2,6-dimethyl-1,4-dihydropyridine-3,5-dicarboxylate Elemental Analysis; $C_{26}H_{26}N_2O_6$. Calcd. (%) C: 67.52, H: 5.67, N: 6.06. Found (%) C: 67.55, H: 5.64, N: 6.02.

m.p.; 122.0°–126.0° C.

IR (cm$^{-1}$); $\nu_{NH}$ 3330, $\nu_{CO}$ 1690, $\nu_{NO_2}$ 1530, 1350.

NMR $\delta_{CDCl_3}$; 1.78(s, 3H), 2.32(s, 3H), 2.36(s, 3H), 3.60(s, 3H), 4.59(s, 2H), 5.14(s, 1H), 6.34(s, 1H), 6.40(s, 1H), 7.0–8.1(m, 9H).

Example 23

1,1-dimethyl-3-phenyl-2-propenyl methyl 4-(3-nitrophenyl)-2,6-dimethyl-1,4-dihydropyridine-3,5-dicarboxylate Elemental Analysis; $C_{27}H_{28}N_2O_6$. Calcd. (%) C: 68.05, H: 5.92, N: 5.88. Found (%) C: 68.10, H: 5.88, N: 5.83.

m.p.; Oily.

IR (cm$^{-1}$); $\nu_{NH}$ 3330, $\nu_{CO}$ 1690, $\nu_{NO_2}$ 1530, 1350.

NMR $\delta_{CDCl_3}$; 1.60(d, 6H), 2.30(s, 6H), 3.51(s, 3H), 5.05(s, 1H), 5.98(s, 1H), 6.30(s, 2H), 7.1–8.2(m, 9H).

Example 24

4-(p-methylthiophenyl)-3-butenylmethyl 4-(3-nitrophenyl)-2,6-dimethyl-1,4-dihydropyridine-3,5-dicarboxylate Elemental Analysis; $C_{27}H_{28}N_2O_6S$. Calcd. (%) C: 63.76, H: 5.54, N: 5.51. Found (%) C: 63.74, H: 5.49, N: 5.48.

m.p.; 54.1°–64.4° C.

IR (cm$^{-1}$); $\nu_{NH}$ 3330, $\nu_{CO}$ 1690, $\nu_{NO_2}$ 1530, 1350.

NMR $\delta_{CDCl_3}$; 2.03(s, 6H), 2.43(s, 3H), 2.67(t, 2H), 3.59(t, 2H), 4.17(t, 2H), 5.10(s, 1H), 6.0–8.15(m, 11H).

Example 25

1-ethyl-3-phenyl-2-propenyl methyl 4-(3-nitrophenyl)-2,6-dimethyl-1,4-dihydropyridine-3,5-dicarboxylate Elemental Analysis; $C_{27}H_{28}N_2O_6$. Calcd. (%) C: 68.05, H: 5.92, N: 5.88. Found (%) C: 68.09, H: 5.90, N: 5.85.

m.p.; Oily.

IR (cm$^{-1}$); $\nu_{NH}$ 3330, $\nu_{CO}$ 1690, $\nu_{NO_2}$ 1530, 1350.

NMR $\delta_{CDCl_3}$; 1.70(t, 9H), 1.70(q, 2H), 2.30(d, 6H), 3.59(s, 3H), 5.09(s, 1H), 5.30(t, 1H), 5.8–6.6(m, 3H), 7.0–8.1(m, 9H).

Example 26

4-(3-thienyl)-3-butenyl methyl 4-(3-nitrophenyl)-2,6-dimethyl-1,4-dihydropyridine-3,5-dicarboxylate Elemental Analysis; $C_{24}H_{24}N_2O_6S$. Calcd. (%) C: 61.53, H: 5.16, N: 5.98. Found (%) C: 61.55, H: 5.13, N: 5.89.

m.p.; 122.1°–127.7° C.

IR (cm$^{-1}$); $\nu_{NH}$ 3340, $\nu_{CO}$ 1690, $\nu_{NO_2}$ 1530, 1350

NMR $\delta_{CDCl_3}$; 2.30(s, 6H), 2.4–2.8(m, 2H), 3.57(d, 3H), 4.12(t, 2H), 5.07(s, 1H), 5.7–8.1(m, 10H).

Example 27

1,3-diphenyl-2-propenyl methyl 4-(3-nitrophenyl)-2,6-dimethyl-1,4-dihydropyridine-3,5-dicarboxylate Elemental Analysis; $C_{31}H_{28}N_2O_6$. Calcd. (%) C: 70.97, H: 5.38, N: 5.34. Found (%) C: 70.94, H: 5.44, N: 5.30.

m.p.; 143°–145.5° C.

IR (cm$^{-1}$); $\nu_{NH}$ 3380, $\nu_{CO}$ 1695, $\nu_{NO_2}$ 1525, 1350

NMR $\delta_{CDCl_3}$; 2.62(s, 6H), 3.60(s, 3H), 5.15(s, 1H), 6.2–6.5(m, 4H), 7.0–8.2(m, 14H).

Example 28

4-(2-pyridyl)-3-butenyl methyl 4-(3-nitrophenyl)-2,6-dimethyl-1,4-dihydropyridine-3,5-dicarboxylate Elemental Analysis; $C_{25}H_{25}N_3O_6$. Calcd. (%) C: 64.79, H: 5.44, N: 9.07. Found (%) C: 64.85, H: 5.39, N: 9.06.

m.p.; Oily.

IR (cm$^{-1}$); $\nu_{NH}$ 3330, $\nu_{CO}$ 1700, $\nu_{NO2}$ 1530, 1350.

NMR $\delta_{CDCl3}$; 2.31(s, 6H), 2.60(t, 2H), 3.57(s, 3H), 4.20(t, 2H), 5.09(s, 1H), 6.4–8.6(m, 9H).

Example 29

3-(2-naphthyl)-2-propenyl methyl 4-(3-nitrophenyl)-2,6-dimethyl-1,4-dihydropyridine-3,5-dicarboxylate Elemental Analysis; $C_{29}H_{26}N_2O_6$. Calcd. (%) C: 69.87, H: 5.26, N: 5.62. Found (%) C: 69.99, H: 5.22, N: 5.57.

m.p.; 149.4°–154.3° C.

IR (cm$^{-1}$); $\nu_{NH}$ 3330, $\nu_{CO}$ 1700, $\nu_{NO2}$ 1530, 1350.

NMR $\delta_{CDCl3}$; 2.30(s, 3H), 2.34(s, 3H), 3.60(s, 3H), 4.74(d, 2H), 5.15(s, 1H), 6.0–6.85(m, 3H), 7.1–8.2(m, 11H).

EXAMPLE 30

1-methyl-3-phenyl-2-propenyl methyl 4-(3-nitrophenyl)-2,6-dimethyl-1,4-dihydropyridine-3,5-dicarboxylate Elemental Analysis: $C_{26}H_{26}N_2O_6$. Calcd. (%) C: 67.52, H: 5.67, N: 6.06. Found (%) C: 67.71, H: 5.66, N: 6.01.

m.p.; Oily.

IR (cm$^{-1}$); $\nu_{NH}$ 3330, $\nu_{CO}$ 1690, $\nu_{NO2}$ 1530, 1350

NMR $\delta_{CDCl3}$; 1.35(m, 3H), 2.30(s, 6H), 3.60(s, 3H), 5.12(s, 1H), 5.45(m, 1H), 6.0–6.8(m, 3H), 7.1–8.2(m, 9H).

Example 31

1-methyl-3-phenyl-2-propenyl ethyl 4-(3-nitrophenyl)-2,6-dimethyl-1,4-dihydropyridine-3,5-dicarboxylate Elemental Analysis; $C_{27}H_{28}N_2O_6$. Calcd. (%) C: 68.05, H: 5.92, N: 5.88. Found (%) C: 68.11, H: 5.88, N: 5.83.

m.p.; Oily.

IR (cm$^{-1}$); $\nu_{NH}$ 3330, $\nu_{CO}$ 1690, $\nu_{NO2}$ 1530, 1350.

NMR $\delta_{CDCl3}$; 1.25(d, 3H), 1.26(q, 3H), 2.30(s, 6H), 4.05(q, 2H), 5.08(s, 1H), 5.37(q, 1H), 5.9–6.7(m, 3H), 7.0–8.15(m, 9H).

Example 32

1-methyl-3-phenyl-2-propenyl isopropyl 4-(3-nitrophenyl)-2,6-dimethyl-1,4-dihydropyridine-3,5-dicarboxylate Elemental Analysis; $C_{28}H_{30}N_2O_6$. Calcd. (%) C: 68.56, H: 6.16, N: 5.71. Found (%) C: 68.60, H: 6.14, N: 5.67. m.p.; Oily.

IR (cm$^{-1}$); $\nu_{NH}$ 3330, $\nu_{CO}$ 1690, $\nu_{NO2}$ 1530, 1350.

NMR $\delta_{CDCl3}$; 1.10(d, 3H), 1.25(d, 6H), 2.32(s, 6H), 4.7–5.2(m, 1H), 5.10(s, 1H), 5.40(q, 1H), 5.9–6.7(m, 3H), 7.1–8.2(m, 9H).

Example 33

1-methyl-3-furyl-3-propenyl methyl 4-(3-nitrophenyl)-2,6-dimethyl-1,4-dihydropyridine-3,5-dicarboxylate Elemental Analysis; $C_{24}H_{24}N_2O_7$. Calcd. (%) C: 63.71, H: 5.35, N: 6.19. Found (%) C: 63.87, H: 5.24, N: 6.11.

m.p.; Oily.

IR (cm$^-$); $\nu_{NH}$ 3330, $\nu_{CO}$ 1680, $\nu_{NO2}$ 1530, 1350.

NMR $\delta_{CDCl3}$; 1.33(dd, 3H), 2.33(s, 6H), 3.62(s, 3H), 5.11(s, 1H), 5.23–5.73(m, 1H), 5.7–6.6(m, 5H), 7.2–8.2(m, 5H).

Example 34

1-methyl-3-phenyl-2-propenyl 2-methoxyethyl 4-(3-nitrophenyl)-2,6-dimethyl-1,4-dihydropyridine-3,5-dicarboxylate Elemental Analysis; $C_{28}H_{30}N_2O_7$. Calcd. (%) C: 66.39, H: 5.97, N: 5.53. Found (%) C: 66.44, H: 5.92, N: 5.47.

m.p.; Oily.

IR (cm$^{-1}$); $\nu_{NH}$ 3330, $\nu_{CO}$ 1690, $\nu_{NO2}$ 1530, 1350.

NMR $\delta_{CDCl3}$; 1.30(d, 3H), 2.30(s, 6H), 3.29(d, 3H), 3.48(t, 2H), 4.15(t, 2H), 5.10(s, 1H), 5.50(q, 1H), 5.9–6.7(m, 3H), 7.0–8.2(m, 9H).

Example 35

2,3-diphenyl-2-propenyl methyl 4-(3-nitrophenyl)-2,6-dimethyl-1,4-dihydropyridine-3,5-dicarboxylate Elemental Analysis; $C_{31}H_{28}N_2O_6$. Calcd. (%) C: 70.98, H: 5.38, N: 5.34. Found (%) C: 71.05, H: 5.37, N: 5.30.

m.p.; Oily.

IR (cm$^{-1}$); $\nu_{NH}$ 3330, $\nu_{CO}$ 1690, $\nu_{NO2}$ 1530, 1350.

NMR $\delta_{CDCl3}$; 2.23(s, 3H), 2.29(s, 3H), 3.60(s, 3H), 4.89(s, 2H), 5.02(s, 1H), 6.0–6.6(m, 3H), 7.0–8.1(m, 10H).

Example 36

1-methyl-3-thienyl-2-propenyl methyl 4-(3-nitrophenyl)-2,6-dimethyl-1,4-dihydropyridine-3,5-dicarboxylate Elemental Analysis; $C_{24}H_{24}N_2O_6S$. Calcd. (%) C: 61.53, H: 5.19, N: 5.98. Found (%) C: 61.55, H: 5.08, N: 5.79.

m.p.; Oily.

IR (cm$^{-1}$); $\nu_{NH}$ 3330, $\nu_{CO}$ 1680, $\nu_{NO2}$ 1525, 1345.

NMR $\delta_{CDCl3}$; 1.37(dd, 3H), 2.33(s, 6H), 3.62(s, 3H), 5.11(s, 1H), 5.23–5.76(m, 1H), 6.48(s, 1H), 5.7–8.2(m, 9H).

Example 37

Cinnamyl methyl 4-(2-furyl)-2,6-dimethyl-1,4-dihydropyridine-3,5-dicarboxylate

Elemental Analysis: $C_{23}H_{23}NO_5$. Calcd. (%) C: 70.21, H: 5.89, N: 3.56. Found (%) C: 70.27, H: 5.84, N: 3.50.

m.p.; Oily.

IR (cm$^{-1}$); $\nu_{NH}$ 3340, $\nu_{CO}$ 1690.

NMR $\delta_{CDCl3}$; 2.28(s, 6H), 3.65(s, 3H), 4.75(dd, 2H), 5.23(s, 1H), 5.88–6.60(m, 5H), 7.1–7.4(m, 6H).

Example 38

Cinnamyl methyl 4-(1-naphthyl)-2,6-dimethyl-1,4-dihydropyridine-3,5-dicarboxylate Elemental Analysis; $C_{29}H_{27}NO_4$. Calcd. (%) C: 76.80, H: 6.00, N: 3.09. Found (%) C: 76.92, H: 5.88, N: 3.01.

m.p.; Oily.

IR (cm$^{-1}$); $\nu_{NH}$ 3330, $\nu_{CO}$ 1690.

NMR $\delta_{CDCl_3}$; 2.23(ss, 6H), 3.54(s, 3H), 4.65(m, 2H), 5.20(s, 1H), 6.0–6.6(m, 3H), 7.0–7.8(m, 12H).

Example 39

4,4-diphenyl-3-butenyl methyl 4-(3-nitrophenyl)-2,6-dimethyl-1,4-dihydropyridine-3,5-dicarboxylate Elemental Analysis; $C_{32}H_{30}N_2O_6$. Calcd. (%) C: 71.36, H: 5.61, N: 5.20. Found (%) C: 71.42, H: 5.53, N: 5.12.

m.p.; Oily.

IR (cm$^{-1}$); $\nu_{NH}$ 3330, $\nu_{CO}$ 1690, $\nu_{NO_2}$ 1530, 1350.

NMR $\delta_{CDCl_3}$; 2.31(s, 6H), 2.48(m, 2H), 3.59(s, 3H), 4.10(t, 2H), 5.10(s, 1H), 5.83(t, 1H), 6.18(s, 1H), 7.03–8.10(m, 14H).

Example 40

Cinnamyl methyl 4-(2-fluorophenyl)-2,6-dimethyl-1,4-dihydropyridine-3,5-dicarboxylate Elemental Analysis; $C_{25}H_{24}FNO_4$. Calcd. (%) C: 71.25, H: 5.74, N: 3.32. Found (%) C: 71.29, H: 5.70, N: 3.28.

m.p.; 73.9°–89.5° C.

IR (cm$^{-1}$); $\nu_{NH}$ 3340, $\nu_{CO}$ 1695.

NMR $\delta_{CDCl_3}$; 2.62(s, 6H), 3.56(s, 3H), 4.5–4.8(m, 2H), 5.28(s, 1H), 6.14(s, 1H), 6.0–7.7(m, 11H).

EXAMPLE 41

434 mg (1 mM) of 4-(3-nitrophenyl)-2,6-dimethyl-1,4-dihydropyridine-3,5-dicarboxylic acid monocinnamyl ester, 226 mg (1.1 mM) of dicyclohexylcarbodiimide, 122 mg (1 mM) of 4-dimethylaminopyridine and 127 mg (1.2 mM) of 2-ethylthioethanol were dissolved in 10 ml of dichloroethane, and refluxed for 2 hours. After the reaction mixture was chilled, insoluble matters were filtered off. The solvent was evaporated under reduced pressure, and the residue was purified by silica gel column chromatography to obtain 511 mg of cinnamyl 2-ethylthioethyl 4-(3-nitrophenyl)-2,6-dimethyl-1,4-dihydropyridine-3,5-dicarboxylate (yield 98%).

Elemental Analysis; $C_{28}H_{30}N_2O_6S$. Calcd. (%) C: 64.35, H: 5.79, N: 5.36. Found (%) C: 64.48, H: 5.62, N: 5.11.

m.p.; 142.5°–143.5° C.

IR (cm$^{-1}$); $\nu_{NH}$ 3320, $\nu_{CO}$ 1695, 1650, $\nu_{NO_2}$ 1530, 1350.

NMR $\delta_{CDCl_3}$; 1.18(t, 3H), 2.32(s, 6H), 2.52(t, 2H), 2.62(q, 2H), 4.14(t, 2H), 4.68(d, 2H), 5.12(s, 1H), 5.9–6.7(m, 3H), 7.1–8.2(m, 9H).

EXAMPLES 42–47

The following 1,4-dihydropyridine derivatives were prepared in the same manner as Example 41, except that 2-ethylthioethanol was changed by the following alcohol.

Example 42

Cinnamyl 2-phenylthioethyl 4-(3-nitrophenyl)-2,6-dimethyl-1,4-dihydropyridine-3,5-dicarboxylate 2-phenylthioethanol: 185 mg (1.2 mM).

Yield; 554 mg (97%).

Elemental Analysis; $C_{32}H_{30}N_2O_6S$. Calcd. (%) C: 67.35, H: 5.30, N: 4.91. Found (%) C: 67.08, H: 5.51, N: 4.77.

m.p.; 120.5°–121.5° C.

IR (cm$^{-1}$); $\nu_{NH}$ 3380, $\nu_{CO}$ 1705, 1640, $\nu_{NO_2}$ 1530, 1350.

NMR $\delta_{CDCl_3}$; 2.32(s, 6H), 3.04(t, 2H), 4.20(t, 2H), 4.18(d, 2H), 5.12(s, 1H), 5.9–6.7(m, 3H), 7.2–8.2(m, 14H).

Example 43

Cinnamyl 2-(N,N-dimethylamino)ethyl 4-(3-nitrophenyl)-2,6-dimethyl-1,4-dihydropyridine-3,5-dicarboxylate 2-(N,N-dimethylamino)ethanol: 107 mg (1.2 mM)

Yield; 526 mg (97%).

Elemental Analysis; $C_{28}H_{32}ClN_3O_6$. Calcd. (%) C: 62.05, H: 5.95, N:7.75. Found (%) C: 62.31, H: 5.76, N: 7.59.

m.p.; Oily.

IR (cm$^{-1}$); $\nu_{NH}$ 3330, $\nu_{CO}$ 1690, $\nu_{NO_2}$ 1530, 1350

NMR $\delta_{CDCl_3}$; 2.16(s, 6H), 2.33(s, 3H), 2.50(t, 2H), 4.10(t, 2H), 4.66(d, 2H), 5.14(s, 1H), 5.9–6.9(m, 3H), 7.1–8.2(m, 9H).

Example 44

Cinnamyl 2-phenoxyethyl 4-(3-nitrophenyl)-2,6-dimethyl-1,4-dihydropyridine-3,5-dicarboxylate 2-phenoxyethanol: 166 mg (1.2 mM).

Yield; 544 mg (98%).

Elemental Analysis; $C_{32}H_{30}N_2O_7$. Calcd. (%) C: 69.30, H: 5.41, N: 5.05. Found (%) C: 69.45, H: 5.27, N: 4.96.

m.p.; Oily.

IR (cm$^{-1}$); $\nu_{NH}$ 3340, $\nu_{CO}$ 1690, $\nu_{NO_2}$ 1530, 1350.

NMR $\delta_{CDCl_3}$; 2.30(s, 6H), 4.02(m, 2H), 4.34(m, 2H), 4.64(d, 2H), 5.14(s, 1H), 5.8–8.2(m, 17H).

Example 45

Dicinnamyl 4-(3-nitrophenyl)-2,6-dimethyl-1,4-dihydropyridine-3,5-dicarboxylate Cinnamyl alcohol: 160 mg (1.2 mM).

Yield; 540 mg (98%).

Elemental Analysis; $C_{33}H_{30}N_2O_6$. Calcd. (%) C: 71.99, H: 5.49, N: 5.09. Found (%) C: 72.08, H: 5.35, N: 5.00.

m.p.; 145°–146° C.

IR (cm$^{-1}$); $\nu_{NH}$ 3360, $\nu_{CO}$ 1690, 1640, $\nu_{NO_2}$ 1520, 1350.

NMR $\delta_{CDCl_3}$; 2.30(s, 6H), 4.66(d, 4H), 5.15(s, 1H), 5.8–6.6(m, 5H), 7.0–8.2(m, 14H).

Example 46

Cinnamyl phenylpropargyl 4-(3-nitrophenyl)-2,6-dimethyl-1,4-dihydropyridine-3,5-dicarboxylate Phenylpropargyl alcohol: 158 mg (1.2 mM).

Yield; 510 mg (93%).
Elemental Analysis; $C_{33}H_{28}N_2O_6$. Calcd. (%) C: 72.25, H: 5.14, N: 5.11. Found (%) C: 72.47, H: 5.06, N: 5.02.
m.p.; 159.5°–160.5° C.
IR (cm$^{-1}$); $\nu_{NH}$ 3360, $\nu_{CO}$ 1690, 1640, $\nu_{NO2}$ 1520, 1350.
NMR $\delta_{CDCl3}$; 2.43(s, 6H), 4.68(d, 2H), 4.83(s, 2H), 5.15(s, 1H), 5.8–6.7(m, 3H), 7.1–8.2(m, 14H).

Example 47

Cinnamyl 1-methyl-3-phenyl-2-propenyl 4-(3-nitrophenyl)-2,6-dimethyl-1,4-dihydropyridine-3,5-dicarboxylate 4-phenyl-3-buten-1-ol: 178 mg (1.2 mM).
Yield; 559 mg (99%).
Elemental Analysis; $C_{34}H_{32}N_2O_6$. Calcd. (%) C: 72.32, H: 5.71, N: 4.96. Found (%) C: 72.51, H: 5.66, N: 4.92.
m.p.; Oily.
IR (cm$^{-1}$); $\nu_{NH}$ 3340, $\nu_{CO}$ 1690, $\nu_{NO2}$ 1530, 1350.
NMR $\delta_{CDCl3}$; 1.35(d, 3H), 2.30(s, 6H), 4.66(d, 2H), 5.12(s, 1H), 5.42(m, 1H), 5.8–6.7(m, 5H), 7.1–8.2(m, 14H).

EXAMPLE 48

332 mg (1 mM) of 4-(3-nitrophenyl)-2,6-dimethyl-3-methoxycarbonyl-1,4-dihydropyridine-5-carboxylic acid, 226 mg (1.1 mM) of dicyclohexylcarbodiimide, 122 mg (1 mM) of 4-dimethylaminopyridine and 238 mg (1.2 mM) of 4-(1-naphthyl)-3-buten-1-ol were dissolved in 10 ml of dichloroethane, and refluxed for 2 hours. After the reaction mixture was chilled, insoluble matters were filtered off. The solvent was evaporated under reduced pressure, and the residue was purified by silica gel chromatography to obtain 507 mg of methyl 4-(1-naphthyl)-3-butenyl 4-(3-nitrophenyl)-2,6-dimethyl-1,4-dihydropyridine-3,5-dicarboxylate (yield 99%).
Elemental Analysis; $C_{30}H_{28}N_2O_6$. Calcd. (%) C: 70.30, H: 5.51, N: 5.47. Found (%) C: 70.33, H: 5.44, N: 5.40.
m.p.; Oily.
IR (cm$^{-1}$); $\nu_{NH}$ 3360, $\nu_{CO}$ 1700, 1650, $\nu_{NO2}$ 1535, 1350.
NMR $\delta_{CDCl3}$; 2.22(s, 6H), 2.57(m, 2H), 3.50(s, 3H), 4.12(m, 2H), 5.05(s, 1H), 5.5–8.1(m, 14H).

EXAMPLES 49–59

The following 1,4-dihydropyridine derivatives were prepared in the same manner as Example 48 except that 4-(1-naphtyl)-3-buten-1-ol was changed by the following alcohol.

Example 49

1,1-dimethyl-4-phenyl-3-butenyl methyl 4-(3-nitrophenyl)-2,6-dimethyl-1,4-dihydropyridine-3,5-dicarboxylate 5-phenyl-2-methyl-4-penten-2-ol: 211 mg (1.2 mM).
Yield; 147 mg (30%).
Elemental Analysis; $C_{28}H_{30}N_2O_6$. Calcd. (%) C: 68.56, H: 6.16, N: 5.71. Found (%) C: 68.77, H: 6.08, N: 5.55.
m.p.; Oily.
IR (cm$^{-1}$); $\nu_{NH}$ 3340, $\nu_{CO}$ 1690, $\nu_{NO2}$ 1530, 1350.
NMR $\delta_{CDCl3}$; 1.42(s, 6H), 2.29(s, 6H), 2.64(d, 2H), 3.56(s, 3H), 5.02(s, 1H), 5.6–6.5(m, 3H), 7.0–8.1(m, 9H).

Example 50

Methyl 5-phenyl-4-pentenyl 4-(3-nitrophenyl)-2,6-dimethyl-1,4-dihydropyridine-3,5-dicarboxylate 5-phenyl-4-penten-1-ol: 194 mg (1.2 mM).
Yield; 462 mg (97%).
Elemental Analysis; $C_{27}H_{28}N_2O_6$. Calcd. (%) C: 68.05, H: 5.92, N: 5.88. Found (%) C: 68.21, H: 5.77, N: 5.81.
m.p.; Oily.
IR (cm$^{-1}$); $\nu_{NH}$ 3330, $\nu_{CO}$ 1690, $\nu_{NO2}$ 1530, 1350.
NMR $\delta_{CDCl3}$; 1.78(m, 2H), 2.17(m, 2H), 2.38(ss, 6H), 3.66(s, 3H), 4.09(m, 2H), 5.11(s, 1H), 5.70(s, 1H), 6.1–6.4(m, 2H), 7.1–8.2(m, 9H).

Example 51

Methyl 5-(2-thienyl)-2,4-pentadienyl 4-(3-nitrophenyl)-2,6-dimethyl-1,4-dihydropyridine-3,5-dicarboxylate 5-(2-thienyl)-2,4-pentadien-1-ol: 199 mg (1.2 mM).
Yield; 457 mg (95%).
Elemental Analysis; $C_{25}H_{24}N_2O_6S$. Calcd. (%) C: 62.49, H: 5.03, N: 5.83. Found (%) C: 62.63, H: 5.11, N: 5.77.
m.p.; 122.8°–154.7° C.
IR (cm$^{-1}$); $\nu_{NH}$ 3300, $\nu_{CO}$ 1700, 1620, $\nu_{NO2}$ 1470, 1355.
NMR $\delta_{CDCl3}$; 2.21(s, 6H), 3.60(s, 3H), 4.57(d, 2H), 5.10(s, 1H), 5.40–8.14(m, 12H).

Example 52

Methyl 5-(2-furyl)-2,4-pentadienyl 4-(3-nitrophenyl)-2,6-dimethyl-1,4-dihydropyridine-3,5-dicarboxylate 5-(2-furyl)-2,4-pentadien-1-ol: 180 mg (1.2 mM).
Yield; 446 mg (96%).
Elemental Analysis; $C_{25}H_{24}N_2O_7$. Calcd. (%) C: 64.65, H: 5.21, N: 6.03. Found (%) C: 64.81, H: 5.03, N: 5.99.
m.p.; 112.2°–113.7° C.
IR (cm$^{-1}$); $\nu_{NH}$ 3300, $\nu_{CO}$ 1695, 1620, $\nu_{NO2}$ 1465, 1350.
NMR $\delta_{CDCl3}$; 2.33(s, 6H), 3.62(s, 3H), 4.61(d, 2H), 5.13(s, 1H), 5.42–6.76(m, 7H), 7.16–8.20(m, 5H).

Example 53

Methyl 5-(2-naphthyl)-2,4-pentadienyl 4-(3-nitrophenyl)-2,6-dimethyl-1,4-dihydropyridine-3,5-dicarboxylate 5-(2-naphthyl)-2,4-pentadien-1-ol: 252 mg (1.2 mM).
Yield; 488 mg (93%).
Elemental Analysis; $C_{30}H_{25}N_2O_6$. Calcd. (%) C: 70.72, H: 4.95, N: 5.50. Found (%) C: 70.90, H: 4.86, N: 5.44.
m.p.; 181.4°–187.6° C.
IR (cm$^{-1}$); $\nu_{NH}$ 3300, $\nu_{CO}$ 1695, 1620, $\nu_{NO2}$ 1460, 1350.
NMR $\delta_{CDCl3}$; 2.32(s, 6H), 3.60(s, 3H), 4.62(d, 2H), 5.11(s, 1H), 5.54–6.95(m, 5H), 7.05–8.20(m, 11H).

Example 54

Methyl 5-(1-naphthyl)-2,4-pentadienyl 4-(3-nitrophenyl)-2,6-dimethyl-1,4-dihydropyridine-3,5-dicarboxylate 5-(1-naphthyl)-2,4-pentadiene-1-ol: 252 mg (1.2 mM).

Yield; 498 mg (95%).
Elemental Analysis; $C_{30}H_{25}N_2O_6$. Calcd. (%) C: 70.72, H: 4.95, N: 5.50. Found (%) C: 70.86, H: 4.89, N: 5.42.
m.p.; 143.8°–147.5° C.
IR (cm$^{-1}$); $\nu_{NH}$ 3300, $\nu_{CO}$ 1695, 1620, $\nu_{NO_2}$ 1460, 1350.
NMR $\delta_{CDCl_3}$; 2.29(s, 3H), 2.33(s, 3H), 3.60(s, 3H), 4.63(d, 2H), 5.16(s, 1H), 5.53–8.43(m, 16H).

Example 55

Methyl phenylpropargyl 4-(3-nitrophenyl)-2,6-dimethyl-1,4-dihydropyridine-3,5-dicarboxylate Phenylpropargyl alcohol: 158 mg (1.2 mM).
Yield; 438 mg (98%).
Elemental Analysis; $C_{25}H_{22}N_2O_6$. Calcd. (%) C: 67.26, H: 4.97, N: 6.27. Found (%) C: 67.36, H: 4.92, N: 6.19.
m.p.; 127°–128° C.
IR (cm$^{-1}$); $\nu_{NH}$ 3360, $\nu_{CO}$ 1690, $\nu_{NO_2}$ 1535, 1350.
NMR $\delta_{CDCl_3}$; 2.32(s, 6H), 3.60(s, 3H), 4.85(s, 2H), 5.12(s, 1H), 6.72(bs, 1H), 7.1"8.2(m, 9H).

Example 56

Methyl (Z)-3-phenyl-2-propenyl 4-(3-nitrophenyl)-2,6-dimethyl-1,4-dihydropyridine-3,5-dicarboxylate (cis)

(Z)-3-phenyl-2-propen-1-ol: 160 mg (1.2 mM).
Yield; 413 mg (92%).
Elemental Analysis; $C_{25}H_{24}N_2O_6$. Calcd. (%) C: 66.95, H: 5.39, N: 6.25. Found (%) C: 67.02, H: 5.31, N: 6.07.
m.p.; 136°–137° C.
IR (cm$^{-1}$); $\nu_{NH}$ 3360, $\nu_{CO}$ 1700, 1650, $\nu_{NO_2}$ 1530, 1350.
NMR $\delta_{CDCl_3}$; 2.30(s, 6H), 3.60(s, 3H), 5.10(s, 1H), 5.70(tt, 1H), 6.56(d, 1H), 6.64(s, 1H), 7.1–8.1(m, 9H).

Example 57

Methyl (Z)-4-(2-naphthyl)-3-butenyl 4-(3-nitrophenyl)-2,6-dimethyl-1,4-dihydropyridine-3,5-dicarboxylate (cis)

(Z)-4-(2-naphthyl)-3-buten-1-ol: 238 mg (1.2 mM).
Yield; 481 mg (94%).
Elemental Analysis; $C_{30}H_{28}N_2O_6$. Calcd. (%) C: 70.30, H: 5.15, N: 5.47. Found (%) C: 70.41, H: 5.03, N: 5.41.
m.p.: 139°–140° C.
IR (cm$^{-1}$); $\nu_{NH}$ 3360, $\nu_{CO}$ 1700, 1650, $\nu_{NO_2}$ 1530, 1350.
NMR $\delta_{CDCl_3}$; 2.28(s, 6H), 2.75(m, 2H), 3.56(s, 3H), 4.14(t, 2H), 5.02(s, 1H), 5.60(tt, 1H), 6.25(s, 1H), 6.60(d, 1H), 7.1–8.2(m, 11H).

Example 58

Methyl (2E,4Z)-5-phenyl-2,4-pentadienyl 4-(3-nitrophenyl)-2,6-dimethyl-1,4-dihydropyridine-3,5-dicarboxylate (2E,4Z)-5-phenyl-2,4-pentadien-1-ol: 192 mg (1.2 mM).
Yield; 427 mg (90%).
Elemental Analysis; $C_{27}H_{26}N_2O_6$. Calcd. (%) C: 68.34, H: 5.52, N: 5.90. Found (%) C: 68.46, H: 5.47, N: 5.88.
m.p.; 108.6°–115.4° C.
IR (cm$^{-1}$); $\nu_{NH}$ 3300, $\nu_{CO}$ 1695, 1620, $\nu_{NO_2}$ 1460, 1355.
NMR $\delta_{CDCl_3}$; 2.16(s, 6H), 3.44(s, 3H), 4.47(d, 2H), 5.00(s, 1H), 5.41–5.95(m, 1H), 5.95–8.10(m, 13H).

Example 59

Methyl (2Z,4E)-5-phenyl-2,4-pentadienyl 4-(3-nitrophenyl)-2,6-dimethyl-1,4-dihydropyridine-3,5-dicarboxylate (2Z,4E)-5-phenyl-2,4-pentadien-1-ol: 192 mg (1.2 mM).
Yield; 413 mg (87%).
Elemental Analysis; $C_{27}H_{26}N_2O_6$. Calcd. (%) C: 68.34, H: 5.52, N: 5.90. Found (%) C: 68.40, H: 5.43, N: 5.82.
m.p.; Oily.
IR (cm$^{-1}$); $\nu_{NH}$ 3300, $\nu_{CO}$ 1695, 1615, $\nu_{NO_2}$ 1460, 1350.
NMR $\delta_{CDCl_3}$; 2.33(s, 6H), 3.56(s, 3H), 4.75(d, 2H), 5.06(s, 1H), 5.43–8.13(m, 14H).

Example 60

346 mg (1 mM) of 4-(3-nitrophenyl)-2,6-dimethyl-3-ethoxycarbonyl-1,4-dihydropyridine-5-carboxylic acid, 226 mg (1.1 mM) of dicyclohexylcarbodiimide, 122 mg (1 mM) of 4-dimethylaminopyridine and 192 mg (1.2 mM) of 5phenyl-2,4-pentadien-1-ol were dissolved in 10 ml of dichloroethane, and refluxed for 2 hours. Thereafter, the reaction mixture was treated in the same manner as Example 48, and 454 mg of ethyl 5-phenyl-2,4-pentadienyl 4-(3-nitrophenyl)-2,6-dimethyl-1,4-dihydropyridine-3,5-dicarboxylate was obtained (yield 93%).
Elemental Analysis; $C_{28}H_{28}N_2O_6$. Calcd. (%) C: 68.84, H: 5.78, N: 5.73. Found (%) C: 68.97, H: 5.72, N: 5.66.
m.p.; 142.7°–146.6° C.
IR (cm$^{-1}$); $\nu_{NH}$ 3300, $\nu_{CO}$ 1695, 1620, $\nu_{NO_2}$ 1565, 1350.
NMR $\delta_{CDCl_3}$; 1.22(t, 3H), 2.36(s, 6H), 4.08(q, 2H), 4.62(d, 2H), 5.12(s, 1H), 5.50–7.02(m, 5H), 7.09–8.18(m, 9H).

EXAMPLES 61–65

The following 1,4-dihydropyridine derivatives were prepared in the same manner as Example 60 except that 4-(3-nitrophenyl)-2,6-dimethyl-3-ethoxycarbonyl-1,4-dihydropyridine-5-carboxylic acid (Examples 61–65) and 5-phenyl-2,4-pentadien-1-ol (Examples 64, 65) were changed.

Example 61

Isopropyl 5-phenyl-2,4-pentadienyl 4-(3-nitrophenyl)-2,6-dimethyl-1,4-dihydropyridine-3,5-dicarboxylate 4-(3-nitrophenyl)-2,6-dimethyl-3-isopropoxycarbonyl-1,4-dihydropyridine-5-carboxylic acid: 360 mg (1 mM).
Yield; 477 mg (95%).
Elemental Analysis; $C_{29}H_{29}N_2O_6$. Calcd. (%) C: 69.45, H: 5.83, N: 5.59 Found (%) C: 69.62, H: 5.72, N: 5.50.
m.p.; 135.5°–136.8° C.
IR (cm$^{-1}$); $\nu_{NH}$ 3300, $\nu_{CO}$ 1690, 1615, $\nu_{NO_2}$ 1465, 1350.
NMR $\delta_{CDCl_3}$; 1.10(d, 3H), 1.25(d, 3H), 2.33(s, 6H), 5.10(d, 2H), 5.50–6.74(m, 5H), 7.10–8.17(m, 9H).

Example 62

2-methoxyethyl 5-phenyl-2,4-pentadienyl 4-(3-nitrophenyl)-2,6-dimethyl-1,4-dihydropyridine-3,5-dicarboxylate 4-(3-nitrophenyl)-2,6-dimethyl-1,4-dihydropyridine-3,5-dicarboxylic acid mono 2-methoxyethyl ester: 376 mg (1 mM).

Yield; 503 mg (97%).

Elemental Analysis; $C_{29}H_{29}N_2O_7$. Calcd. (%) C: 67.30, H: 5.65, N: 5.41. Found (%) C: 67.41, H: 5.60, N: 5.29.

m.p.; Oily.

IR (cm$^{-1}$); $\nu_{NH}$3300, $\nu_{CO}$1695, 1620, $\nu_{NO_2}$1465, 1355.

NMR $\delta_{CDCl_3}$; 2.34(s, 6H), 3.29(s, 3H), 3.37–3.70(m, 2H), 4.05–4.30(m, 2H), 4.49(d, 2H), 5.12(s, 1H), 5.50–6.72(m, 5H), 7.08–8.16(m, 9H).

Example 63

Bis(5-phenyl-2,4-pentadienyl 4-(3-nitrophenyl)-2,6-dimethyl-1,4-dihydropyridine-3,5-dicarboxylate 4-(3-nitrophenyl)-2,6-dimethyl-1,4-dihydropyridine-3,5-dicarboxylic acid 3-(5-phenyl-2,4-pentadienyl)ester: 460 mg (1 mM).

Yield; 567 mg (94%).

Elemental Analysis; $C_{37}H_{34}N_2O_6$. Calcd. (%) C: 73.74, H: 5.69, N: 4.65. Found (%) C: 73.88, H: 5.60, N: 4.59.

m.p.; 152.8°–154.3° C.

IR (cm$^{-1}$); $\nu_{NH}$3320, $\nu_{CO}$1695, 1615, $\nu_{NO_2}$1465, 1350.

NMR $\delta_{CDCl_3}$; 2.29(s, 6H), 4.08(d, 4H), 5.16(s, 1H), 5.37–6.82(m, 9H), 6.87–8.20(m, 14H).

Example 64

Cinnamyl methyl 4-(2-pyridyl)-2,6-dimethyl-1,4-dihydropyridine-3,5-dicarboxylate 4-(2-pyridyl)-2,6-dimethyl-3-methoxycarbonyl-1,4-dihydropyridine-5-carboxylic acid: 294 mg (1 mM).

Cinnamyl alcohol: 161 mg (1.2 mM).

Yield; 356 mg (88%).

Elemental Analysis; $C_{24}H_{24}N_2O_4$. Calcd. (%) C: 76.80, H: 6.00, N: 3.09. Found (%) C: 76.84, H: 5.92, N: 3.05.

m.p.; Oily.

IR (cm$^{-1}$); $\nu_{NH}$3330, $\nu_{CO}$1690.

NMR $\delta_{CDCl_3}$; 2.22(s, 3H), 2.25(s, 3H), 3.56(s, 3H), 4.65(dd, 2H), 5.20(s, 1H), 6.08–6.53(m, 3H), 7.1–7.7(m, 12H).

Example 65

Cinnamyl methyl 4-(2-thienyl)-2,6-dimethyl-1,4-dihydropyridine-3,5-dicarboxylate 4-(2-thienyl)-2,6-dimethyl-3-methoxycarbonyl-1,4-dihydropyridine-5-carboxylic acid: 299 mg (1 mM).

Cinnamyl alcohol: 161 mg (1.2 mM).

Yield; 319 mg (78%).

Elemental Analysis; $C_{23}H_{23}NO_4S$. Calcd. (%) C: 67.46, H: 5.66, N: 3.42. Found (%) C: 67.64, H: 5.32, N: 3.34.

IR (cm$^{-1}$); $\nu_{NH}$3330, $\nu_{CO}$1690.

NMR $\delta_{CDCl_3}$; 2.30(s, 6H), 3.65(s, 3H), 4.75(m, 2H), 5.23(s, 1H), 5.85–6.6(m, 3H), 7.1–7.5(m, 8H).

EXAMPLE 66

664 mg (2 mM) of 4-(3-nitrophenyl)-2,6-dimethyl-1,4-dihydropyridine-3,5dicarboxylic acid 3-methyl ester, 206 mg (2.1 mM) of 2,4-hexadien-1-ol, 433 mg (2.1 mM) of dicyclohexylcarbodiimide and 257 mg (2.1 mM) of 4-dimethylaminopyridine were dissolved in 20 ml of dichloroethane, and refluxed for 2 hours. Insoluble matters were filtered off, and the solvent was evaporated under reduced pressure. The residue was purified by silica gel chromatography, and 734 mg of methyl 2,4-hexadienyl 4-(3-nitrophenyl)-2,6-dimethyl-1,4-dihydropyridine-3,5-dicarboxylate was obtained (yield 89%).

Elemental Analysis; $C_{22}H_{24}N_2O_6$. Calcd. (%) C: 64.07, H: 5.87, N: 6.79. Found (%) C: 64.14, H: 5.82, N: 6.76.

m.p.; 135°–136.5° C.

NMR $\delta_{CDCl_3}$; 1.72(d, 3H), 2.34(s, 6H), 3.62(s, 3H), 4.52(d, 2H), 5.3–6.4(m, 5H), 7.2–8.1(m, 4H).

EXAMPLES 67–71

The following 1,4-dihydropyridine derivatives were prepared in the same manner as Example 66 except that 4-(3-nitrophenyl)-2,6-dimethyl-1,4-dihydropyridine-3,5-dicarboxylic acid 3-methyl ester was changed by the following ester.

Example 67

Ethyl 2,4-hexadienyl 4-(3-nitrophenyl)-2,6-dimethyl-1,4-dihydropyridine-3,5-dicarboxylate 4-(3-nitrophenyl)-2,6-dimethyl-1,4-dihydropyridine-3,5-dicarboxylic acid 3-ethyl ester: 692 mg (2 mM).

Yield; 734 mg (86.1%).

Elemental Analysis; $C_{23}H_{26}N_2O_6$. Calcd. (%) C: 64.78, H: 6.15, N: 6.57. Found (%) C: 64.89, H: 6.03, N: 6.76.

m.p.; 114.7°–115.6° C.

NMR $\delta_{CDCl_3}$; 1.20(t, 3H), 1.72(d, 3H), 2.32(s, 3H), 4.06(q, 2H), 4.51(d, 2H), 5.07(s, 1H), 5.2–6.4(m, 5H), 7.1–8.1(m, 4H).

Example 68

Isopropyl 2,4-hexadienyl 4-(3-nitrophenyl)-2,6-dimethyl-1,4-dihydropyridine-3,5-dicarboxylate 4-(3-nitrophenyl)-2,6-dimethyl-1,4-dihydropyridine-3,5-dicarboxylic acid 3-isopropyl ester: 721 mg (2mM).

Yield; 801 mg (91%).

Elemental Analysis; $C_{24}H_{28}N_2O_6$. Calcd. (%) C: 65.44, H: 6.41, N: 6.36. Found (%) C: 65.61, H: 6.28, N: 6.26.

m.p.; 102.8°–104.3° C.

NMR $\delta_{CDCl_3}$; 1.08(d, 3H), 1.25(d, 3H), 1.75(d, 3H), 2.33(s, 6H), 4.54(d, 2H), 5.00(q, 1H), 5.08(s, 1H), 5.2–6.4(m, 5H), 7.2–8.2(m, 4H).

Example 69

2-methoxyethyl 2,4-hexadienyl 4-(3-nitrophenyl)-2,6-dimethyl-1,4-dihydropyridine-3,5-dicarboxylate 4-(3-nitrophenyl)-2,6-dimethyl-1,4-dihydropyridine-3,5-dicarboxylic acid 3-(2-methoxyethyl)ester: 753 mg (2 mM).

Yield; 754 mg (82.6%).

Elemental Analysis; Calcd. (%) C: 63.15, H: 6.18, N: 6.14. Found (%) C: 63.20, H: 5.98, N: 6.23.

m.p.; 97.3°–98.5° C.

NMR $\delta_{CDCl_3}$; 1.71(d, 3H), 2.32(s, 6H), 3.51(t, 2H), 4.16(t, 2H), 4.50(d, 2H), 5.10(s, 1H), 5.2–6.4(m, 5H), 7.1–8.2(m, 4).

Example 70

Cyclohexyl 2,4-hexadienyl 4-(3-nitrophenyl)-2,6-dimethyl-1,4-dihydropyridine-3,5-dicarboxylate 4-(3-nitrophenyl)-2,6-dimethyl-1,4-dihydropyridine-3,5-dicarboxylic acid 3-cyclohexyl ester: 799 mg (2 mM).

Yield; 868 mg (90.3%).

Elemental Analysis; $C_{27}H_{32}N_2O_6$. Calcd. (%) C: 67.48, H: 6.71, N: 5.83. Found (%) C: 67.62, H: 6.49, N: 5.76.

NMR $\delta_{CDCl_3}$; 0.9–2.1(m, 10H), 1.73(d, 3H), 2.31(s, 6H), 4.4–4.9(m, 1H), 4.51(d, 2H), 5.08(s, 1H), 5.2–6.4(m, 4H), 6.77(s, 1H), 7.1–8.2(m, 4H).

Example 71

Cinnamyl 2,4-hexadienyl 4-(3-nitrophenyl)-2,6dimethyl-1,4-dihydropyridine-3,5-dicarboxylate 4-(3-nitrophenyl)-2,6-dimethyl-1,4-dihydropyridine-3,5-dicarboxylic acid 3-cinnamyl ester: 868 mg (2 mM).

Yield; 926 mg (90%)

Elemental Analysis; $C_{30}H_{30}N_2O_6$. Calcd. (%) C: 70.02, H: 5.88, N: 5.44. Found (%) C: 70.21, H: 5.68, N: 5.26.

m.p. 141°–142° C.

NMR $\delta_{CDCl_3}$; 1.67(d, 3H), 2.31(s, 6H), 4.50(d, 2H), 4.68(d, 2H), 5.16(s, 1H), 5.2–6.9(m, 7H), 7.1–8.2(m, 9H).

EXAMPLE 72

338 mg (1 mM) of 2-(3-trifluoromethylbenzylidene)acetoacetic acid (2,4-hexadienyl) ester was mixed with 138 mg (1.2 mM) of aminocrotonic acid methyl ester, and the mixture was allowed to react at 120° C. for 3 hours. The reaction mixture was purified by silica gel column chromatography, and 279 mg of methyl 2,4-hexadienyl 4-(3-trifluoromethylphenyl)-2,6-dimethyl-1,4-dihydropyridine-3,5-dicarboxylate was obtained (yield 64%).

Elemental Analysis; $C_{23}H_{24}F_3NO_6$. Calcd. (%) C: 59.10, H: 5.18, N: 3.00. Found (%) C: 59.23, H: 5.11, N: 2.87.

m.p.; 129.5°–131.1° C.

NMR $\delta_{CDCl_3}$; 1.73(d, 3H), 2.30(s, 6H), 4.51(d, 2H), 5.03(s, 1H), 5.2–6.3(m, 5H), 7.1–7.6(m, 4H).

EXAMPLE 73

398 mg (1 mM) of 4-(3-nitrophenyl)-2,6-dimethyl-1,4-dihydropyridine-3,5-dicarboxylic acid 3-(2,4-hexadienyl)ester, 108 mg (1.1 mM) of 2,4-hexadien-1-ol, 227 mg (1.1 mM) of dicyclohexylcarbodiimide and 134 mg (1.1 mM) of 4-dimethylaminopyridine were dissolved in 20 ml of dichloroethane, and refluxed for 2 hours. Insoluble matters were filtered off, and the solvent was evaporated under reduced pressure. The residue was purified by silica gel column chromatography, and 428 mg (89.4%) of bis(2,4-hexadienyl) 4-(3-nitrophenyl)-2,6-dimethyl-1,4-dihydropyridine-3,5-dicarboxylate was obtained (yield 89.4%).

Elemental Analysis; $C_{27}H_{30}N_2O_6$. Calcd. (%) C: 67.77, H: 6.32, N: 5.85. Found (%) C: 67.91, H: 6.19, N: 5.71.

m.p.; 145.1°–146.1° C.

NMR $\delta_{CDCl_3}$; 1.71(d, 6H), 2.30(s, 6H), 4.51(d, 4H), 5.1(s, 1H), 5.2–6.4(m, 8H), 6.60(s, 1H), 7.2–8.2(m,4H).

EXAMPLE 74

332 mg (1 mM) of 4-(3-nitrophenyl)-2,6-dimethyl-1,4-dihydropyridine-3,5-dicarboxylic acid 3-methyl ester, 213 mg (1.1 mM) of 4-(2,6,6-trimethyl-1-cyclohexene-1-yl)-3-buten-2-ol, 103 mg (1.1 mM) of dicyclohexylcarbodiimide and 124 mg (1.1 mM) of 4-dimethylaminopyridine were dissolved in 20 ml of dichloroethane, and refluxed for 2 hours. Insoluble matters were filtered off, and the solvent was evaporated under reduced pressure. The residue was purified by silica gel column chromatography, and 468 mg of oily methyl 2-{4-(2,6,6-trimethyl-1-cyclohexene-1-yl)-3-butenyl} 4-(3-nitrophenyl)-2,6-dimethyl-1,4-dihydropyridine-3,5-dicarboxylate was obtained (yield 92.1%).

Elemental Analysis; $C_{29}H_{36}N_2O_6$. Calcd. (%) C: 68.48, H: 7.13, N: 5.51. Found (%) C: 68.59, H: 6.99, N: 5.36.

NMR $\delta_{CDCl_3}$; 0.68–2.30(m, 9H), 0.95(s, 3H), 0.98(s, 3H), 1.63(s, 3H), 2.34(s, 6H), 3.62(s, 3H), 5.09(s, 1H), 5.20–6.25(m, 3H), 6.30(s, 1H), 7.10–8.16(m, 4H).

EXAMPLE 75

199 mg (0.5 mM) of 4-(3-nitrophenyl)-2,6-dimethyl-1,4-dihydropyridine-3,5-dicarboxylic acid mono (2,4-hexadienyl) ester, 44 mg (0.6 mM) of tert-butanol, 113 mg (0.55 mM) of dicyclohexylcarbodiimide and 61 mg (0.5 mM) of 4-dimethylaminopyridine were dissolved in 5 ml of dichloroethane, and refluxed for 2 hours. After the reaction mixture was chilled, insoluble matters were filtered off. The solvent was evaporated under reduced pressure, and the residue was purified by silicas gel column chromatography to obtain 198 mg of a crude material. This material was recrystallized with methanol, and 166 mg of tert-butyl 2,4-hexadienyl 4-(3-nitrophenyl)-2,6-dimethyl-1,4-dihydropyridine-3,5-dicarboxylate was obtained (yield 73%).

Elemental Analysis; $C_{25}H_{30}N_2O_6$. Calcd. (%) C: 66.06, H: 6.65, N: 6.16. Found (%) C: 66.23, H: 6.48, N: 6.09.

m.p.; 151.8°–154.1° C.

IR (cm$^{-1}$); $\nu_{NH}$3340, $\nu_{co}$1700, $\nu_{NO_2}$1530, 1350.

NMR $\delta_{CDCl_3}$; 1.40(s, 9H), 1.72(d, 3H), 2.30(s, 6H), 4.50(d, 2H), 5.01(s, 1H), 5.2–6.3(m, 5H), 7.2–8.2(m, 4H).

EXAMPLES 76–85

The following 1,4-dihydropyridine derivatives were prepared in the same manner as Example 75 except that tert-butanol was changed by the following alcohol.

Example 76

Isobutyl 2,4-hexadienyl 4-(3-nitrophenyl)-2,6-dimethyl-1,4-dihydropyridine-3,5-dicarboxylate 2-methyl-1-propanol: 44 mg (0.6 mM).

Yield; 174 mg (76.6%).

Elemental Analysis; $C_{25}H_{30}N_2O_6$. Calcd. (%) C: 66.06, H: 6.65, N: 6.16. Found (%) C: 66.16, H: 6.59, N: 6.14.

m.p.; 136.4°–137.3° C.

IR (cm$^{-1}$); $\nu_{NH}$ 3330, $\nu_{CO}$ 1705, 1695, $\nu_{NO2}$ 1535, 1350.

NMR $\delta_{CDCl3}$; 0.82(dd, 6H), 1.71(d, 3H), 1.6–2.0(m, 1H), 2.33(s, 6H), 3.82(d, 2H), 4.55(d, 2H), 5.13(s, 1H), 5.2–6.3(m, 4H), 6.57(bs, 1H), 7.2–8.2(m, 4H).

Example 77

2-methyl-2-propen-1-yl 2,4-hexadienyl 4-(3-nitrophenyl)-2,6-dimethyl-1,4-dihydropyridine-3,5-dicarboxylate 2-methyl-2-propen-1-ol: 43 mg (0.6 mM).
Yield; 180 mg (79.6%).
Elemental Analysis; $C_{25}H_{28}N_2O_6$. Calcd. (%) C: 66.36, H: 6.24, N: 6.19. Found (%) C: 66.21, H: 6.11, N: 6.12.
m.p.; 130.6°–131.6° C.
IR (cm$^{-1}$); $\nu_{NH}$ 3330, $\nu_{CO}$ 1705, 1695, $\nu_{NO2}$ 1530, 1350.

NMR $\delta_{CDCl3}$; 1.63(s, 3H), 1.71(d, 3H), 2.33(s, 6H), 4.47(s, 2H), 4.55(d, 2H), 4.80(s, 2H), 5.16(s, 1H), 5.2–6.4(m, 4H), 6.63(bs, 1H), 7.15–8.2(m, 4H).

Example 78

2-butenyl 2,4-hexadienyl 4-(3-nitrophenyl)-2,6-dimethyl-1,4-dihydropyridine-3,5-dicarboxylate Crotyl alcohol: 43 mg (0.6 mM).
Yield; 156 mg (69.0%).
Elemental Analysis; $C_{25}H_{28}N_2O_6$. Calcd. (%) C: 66.36, H: 6.24, N: 6.19. Found (%) C: 66.53, H: 6.07, N: 6.12.
m.p.; 114.8°–116.9° C.
IR (cm$^{-1}$); $\nu_{NH}$ 3340, $\nu_{CO}$ 1705, 1690, $\nu_{NO2}$ 1535, 1355.

NMR $\delta_{CDCl3}$; 1.5–1.75(m, 6H), 2.32(s, 6H), 4.3–4.7(m, 4H), 5.10(s, 1H), 5.2–6.3(m, 6H), 6.41(bs, 1H), 7.15–8.2(m, 4H).

Example 79

3-butenyl 2,4-hexadienyl 4-(3-nitrophenyl)-2,6-dimethyl-1,4-dihydropyridine-3,5-dicarboxylate 3-buten-1-ol: 43 mg (0.6 mM).
Yield; 116 mg (51.3%).
Elemental Analysis; $C_{25}H_{28}N_2O_6$. Calcd. (%) C: 66.36, H: 6.24, N: 6.19. Found (%) C: 66.51, H: 6.17, N: 6.08.
m.p.; 83°–83.6° C.
IR (cm$^{-1}$); $\nu_{NH}$ 3340, $\nu_{CO}$ 1705, 1690, $\nu_{NO2}$ 1535, 1350.

NMR $\delta_{CDCl3}$; 1.70(d, 3H), 2.31(m, 8H), 4.10(t, 2H), 4.53(d, 2H), 4.8–6.3(m, 8H), 6.64(bs, 1H), 7.1–8.2(m, 4H).

Example 80

Allyl 2,4-hexadienyl 4-(3-nitrophenyl)-2,6-dimethyl-1,4-dihydropyridine-3,5-dicarboxylate Allyl alcohol: 35 mg (0.6 mM).
Yield; 144 mg (65.7%).
Elemental Analysis; $C_{24}H_{26}N_2O_6$. Calcd. (%) C: 65.44, H: 6.41, N: 6.36. Found (%) C: 65.52, H: 6.36, N: 6.27.
m.p.; 93.2°–101.4° C.
IR (cm$^{-1}$); $\nu_{NH}$ 3330, $\nu_{CO}$ 1700, 1690, $\nu_{NO2}$ 1530, 1350.

NMR $\delta_{CDCl3}$; 1.75(d, 3H), 2.35(s, 6H), 4.58(d, 2H), 4.95–6.5(m, 8H), 6.90(bs, 1H), 7.2–8.25(m, 4H).

Example 81

Benzyl 2,4-hexadienyl 4-(2-furyl)-2,6-dimethyl-1,4-dihydropyridine-3,5-dicarboxylate Benzyl alcohol: 65 mg.
Recrystallized with acetonitrile instead of methanol
Yield; 224 mg (91.7%).
Elemental Analysis; $C_{28}H_{28}N_2O_6$. Calcd. (%) C: 68.84, H: 5.78, N: 5.73. Found (%) C: 69.03, H: 5.72, N: 5.64.
m.p.; 173.3°–175.2° C.
IR (cm$^{-1}$); $\nu_{NH}$ 3330, $\nu_{CO}$ 1705, 1690, $\nu_{NO2}$ 1530, 1355.

NMR $\delta_{CDCl3}$; 1.70(d, 3H), 2.27(s, 6H), 4.35–4.7(m, 2H), 5.03(d, 2H), 5.13(s, 1H), 5.2–6.4(m, 4H), 6.86(bs, 1H), 7.0–8.15(m, 9H).

Example 82

1-methyl-2-propenyl 2,4-hexadienyl 4-(3-nitrophenyl)-2,6-dimethyl-1,4-dihydropyridine-3,5-dicarboxylate 3-buten-2-ol: 43 mg.
Recrystallization was not carried out.
Yield; 236 mg (100%).
Elemental Analysis; $C_{25}H_{28}N_2O_6$. Calcd. (%) C: 66.36, H: 6.24, N: 6.19. Found (%) C: 66.57, H: 6.08, N: 6.24.
m.p.; Oily.
IR (cm$^{-1}$); $\nu_{NH}$ 3340, $\nu_{CO}$ 1700, 1690, $\nu_{NO2}$ 1530, 1350.

NMR $\delta_{CDCl3}$; 1.26(dd, 3H), 1.71(d, 3H), 2.30(s, 6H), 4.53(d, 2H), 4.7–6.4(m, 8H), 6.80(bs, 1H), 7.2–8.2(m, 4H).

Example 83 n-butyl 2,4-hexadienyl 4-(3-nitrophenyl)-2,6-dimethyl-1,4-dihydropyridine-3,5-dicarboxylate n-butanol: 44 mg.
Yield; 203 mg (89.3%).
Elemental Analysis; $C_{25}H_{30}N_2O_6$. Calcd. (%) C: 66.06, H: 6.65, N: 6.16. Found (%) C: 66.17, H: 6.43, N: 6.07.
m.p.; 105.5°–106.7° C.
IR (cm$^{-1}$); $\nu_{NH}$ 3340, $\nu_{CO}$ 1705, 1690, $\nu_{NO2}$ 1530, 1350.

NMR $\delta_{CDCl3}$; 0.6–1.05(m, 3H), 1.05–1.80(m, 4H), 1.70(d, 3H), 2.31(s, 6H), 4.02(t, 2H), 4.05(d, 2H), 5.12(s, 2H), 5.25–6.3(m, 4H), 6.8–8.2(m, 5H).

Example 84 n-propyl 2,4-hexadienyl 4-(3-nitrophenyl)-2,6-dimethyl-1,4-dihydropyridine-3,5-dicarboxylate n-propanol: 36 mg.
Yield; 147 mg (66.7%).
Elemental Analysis; $C_{24}H_{28}N_2O_6$. Calcd. (%) C: 65.44, H: 6.41, N: 6.36. Found (%) C: 65.60, H: 6.27, N: 6.31.
m.p.; 112.8°–114.5° C.
IR (cm$^{-1}$); $\nu_{NH}$ 3330, $\nu_{CO}$ 1705, 1690, $\nu_{NO2}$ 1530, 1350.

NMR $\delta_{CDCl_3}$; 0.84(t, 3H), 1.52(m, 2H), 2.33(s, 6H), 3.99(t, 2H), 4.53(d, 2H), 5.12(s, 1H), 5.2-6.4(m, 4H), 6.55(bs, 1H), 7.2-8.2(m, 4H).

Example 85

Cyclopropylmethyl 2,4-hexadienyl 4-(3-nitrophenyl)-2,6-dimethyl-1,4-dihydropyridine-3,5-dicarboxylate Cyclopropyl carbinol: 43 mg.
Yield; 86 mg (38%).
Elemental Analysis; $C_{25}H_{28}N_2O_6$. Calcd. (%) C: 66.36, H: 6.24, N: 6.19. Found (%) C: 66.28, H: 6.29, N: 6.12.
m.p.; 119.6°-120.8° C.
IR (cm$^{-1}$); $\nu_{NH}$ 3340, $\nu_{CO}$ 1705, 1690, $\nu_{NO_2}$ 1535, 1350
NMR $\delta_{CDCl_3}$; 0.08-0.7(m, 4H), 0.7-1.5(m, 1H), 1.70(d, 3H), 2.31(s, 6H), 3.84(d, 2H), 4.51(d, 2H), 5.10(s, 1H), 5.2-6.6(m, 5H), 7.15-8.2(m, 4H).

EXAMPLE 86

Using 235 mg (2.1 mM) of 2,4-heptadien-1-ol instead of 2,4-hexadien-1-ol, methyl 2,4-heptadienyl 4-(3-nitrophenyl)-2,6-dimethyl-1,4-dihydropyridine-3,5-dicarboxylate was prepared in the same manner as Example 66.
Yield; 820 mg (96%).
Elemental Analysis; $C_{23}H_{26}N_2O_6$. Calcd. (%) C: 64.78, H: 6.15, N: 6.57. Found (%) C: 64.91, H: 6.02, N: 6.47.
m.p.; Oily.
IR (cm$^{-1}$); $\nu_{NH}$ 3330, $\nu_{CO}$ 1685, $\nu_{NO_2}$ 1530, 1350.
NMR $\delta_{CDCl_3}$; 1.00(t, 3H), 2.10(m, 2H), 2.34(s, 6H), 3.62(s, 3H), 4.55(d, 2H), 5.10(s, 1H), 5.3-6.3(m, 5H), 7.2-8.2(m, 4H).

EXAMPLE 87

Male spontaneously hypertensive rats (SHR) which had mean arterial blood pressures higher than 140 mmHg were used for the experiments. Arterial blood pressure was measured through the catherized artery with a pressure transducer (MPU-0.5, manufactured by Nihon Kohden Kabushiki Kaisha). The catheter was inserted into the abdominal aorta via the median coccygcal artery of SHR under light ether anesthesia. The recordings were made on a rectigraph (manufactured by Sanei Sokki Kabushiki Kaisha). The 1,4-dihydropyridine derivatives prepared in the foregoing examples were administered with catheter which was inserted previously into the caudal vein or duodenum at least two hours after the operation. SHR were restrained with wire mesh cage immediately after the operation. Each derivative to be tested was dissolved in 1.5% PVP/ethanol, and then diluted with 0.9% saline or intravenous administration (30 μg/kg), or suspended in 5% gum arabic solution of intraduodenal administration (1 mg/kg).

The results of the intravenous administration are shown in the following table.

TABLE 1

| Derivatives of the Invention Ex. No. | ΔBP*[1] mmHg | The time to reach the lowest BP min | Duration min |
|---|---|---|---|
| 1 (trans) | 44 | 1.7 | 90< |
| 4 | 63.3 | 1.3 | 90< |
| 5 | 44 | 1.0 | 65 |
| 6 | 55 | 70 | 90< |

TABLE 1-continued

| Derivatives of the Invention Ex. No. | ΔBP*[1] mmHg | The time to reach the lowest BP min | Duration min |
|---|---|---|---|
| 8 | 87 | 25 | 180< |
| 9 | 12 | 13 | 240< |
| 10 | 72 | 12.5 | 90< |
| 11 | 60 | 1.6 | 100 |
| 12 (trans) | 50 | 3.0 | 90< |
| 13 | 35 | 2.0 | 270< |
| 17 | 70 | 1.0 | 80< |
| 20 | 52.5 | 1.8 | 90 |
| 21 | 70 | 1.0 | 120< |
| 22 | 50 | 1.8 | 120 |
| 23 | 48 | 2.2 | — |
| 24 | 60 | 2.1 | 120 |
| 25 | 71 | 10 | 240< |
| 26 | 47 | 1.5 | — |
| 27 | 45 | 56 | 240< |
| 29 | 25 | 5.0 | — |
| 30 | 75 | 5.0 | 120< |
| 31 | 73 | 40 | 170< |
| 32 | 90 | 5 | 190< |
| 33 | 85 | 10.0 | 240< |
| 34 | 45 | 5 | 230< |
| 36 | 69 | 25.0 | 220< |
| 40 | 60 | 1.4 | 90< |
| 41 | 28 | 5 | 120< |
| 42 | 35 | 10 | 90< |
| 44 | 43 | 7 | (45) |
| 45 | 32 | 27 | 90< |
| 46 | 20 | 20 | — |
| 47 | 67 | 48 | 120< |
| 50 | 64 | 2 | 90< |
| 51 | 40 | 2.0 | 90< |
| 52 | 55 | 2.0 | 90< |
| 53 | 25 | 18 | 90 |
| 54 | 30 | 6.0 | 90< |
| 55 | 55 | 2 | 90< |
| 56 | 40.3 | 1.3 | — |
| 57 | 26.8 | 2.6 | — |
| 58 | 64 | 1.9 | — |
| 59 | 56.7 | 1.8 | — |
| 60 | 60 | 4.0 | 90< |
| 61 | 85 | 7.0 | 90< |
| 62 | 60 | 2.0 | 90< |
| 65 | 18 | 0.3 | — |
| 66 | 71.7 | 1.4 | (43.3) 90< |
| 67 | 72 | 1.0 | (37) 90< |
| 68 | 60 | 1.4 | (13) 90< |
| 69 | 60 | 1.0 | 90< |
| 70 | 65 | 7.0 | 90< |
| 71 | 42 | 10 | 90< |
| 72 | 63 | 1.5 | 120< |
| 73 | 55 | 6.0 | 120< |
| 74 | 75 | 20 | 120< |
| 75 | 28 | 1 | — |
| 76 | 32 | 6 | — |
| 77 | 60 | 2 | — |
| 78 | 23 | 2.4 | — |
| 79 | 55 | 2.7 | — |
| 80 | 40 | 1.4 | — |
| 81 | 25 | 2.0 | — |
| 83 | 45 | 2.6 | — |
| 84 | 35 | 2 | — |
| 85 | 35 | 2.6 | — |
| A | 18.7 | 0.9 | 35.6 ± 6.5 |
| B | 58.3 | 0.6 | 45-90 |

*[1]Maximum depressor response
A Nifedipine
B Nicardipine
The number in parentheses indicates half-life.

The results of the intraduodenal administration are shown in the following table.

TABLE 2

| Derivatives of the Invention Ex. No. | ΔBP*[1] mmHg | The time to reach the lowest BP min. | Half-life min. |
|---|---|---|---|
| 1 (trans) | 35.0 | 43.7 | 120< |

TABLE 2-continued

| Derivatives of the Invention Ex. No. | ΔBP*1 mmHg | The time to reach the lowest BP min. | Half-life min. |
|---|---|---|---|
| 4 | 20 | 105 | 170< |
| 7 | 20 | 105 | 120< |
| 11 | 25 | 200 | 240 |
| 12 (trans) | 25 | 50 | 100 |
| 15 | 45 | 75 | 120< |
| 16 | 45 | 50 | 120< |
| 17 | 25 | 180 | 200< |
| 18 | 18 | 37 | 120 |
| 24 | 27 | 160 | 160< |
| 27 | 82 | 170 | 240< |
| 30 | 89 | 65 | 240< |
| 33 | 100 | 22 | 240< |
| 36 | 59 | 130 | 240< |
| 55 | 45 | 60 | 240< |
| 66 | 65 | 35 | 120< |
| A | 48.3 | 6.0 | 20.0 |
| B | 35 | 10.7 | 46.7 |
| C | 20 | 8 | 20.0 |
| D | 0 | — | — |
| E | 0 | — | — |

C: 4-(3-nitrophenyl)-2,6-dimethyl-1,4-dihydropyridine-3,5-dicarboxylic acid 3-methyl ester 5-allyl ester
D: 4-(3-nitrophenyl)-2,6-dimethyl-1,4-dihydropyridine-3,5-dicarboxylic acid 3-methyl ester 5-propargyl ester
E: 4-(3-nitrophenyl)-2,6-dimethyl-1,4-dihydropyridine-3,5-dicarboxylic acid 3-methyl ester 5-(3-phenyl)-1-propyl ester Acute toxicity of several derivatives was tested with male ddy mice weighed 15–30 grams by the up and down method. Each derivative was dissolved in 1.5% PVP/ethanol solution, and diluted with a saline solution. Such derivative solution was injected into the caudal vein, and the acute toxicity was determined.

The result are shown in the following table.

TABLE 3

| Derivatives of the Invention Ex. No. | $LD_{50}$ mg/kg |
|---|---|
| 1 (trans) | 150< |
| 1 (cis) | 150< |
| 7 | 60< |
| 12 (trans) | 60< |
| 12 (cis) | 75< |
| 17 | 45 |
| 24 | 50 |
| 55 | 60< |
| A | 5 |
| B | 9.7 |

EXAMPLE 88

Male SHR which has systolic blood pressure higher than 160 mmHg were used in conscious for the experiments. Systolic blood pressure was measured by the tail cuff method with electrophygmomanometer (PE-300, made by Narco Co.). Each derivative (3 mg/kg) was administered orally, suspended in 5% gum arabic solution.

The results are shown in the following table.

TABLE 4

| Derivatives of the Invention Ex. No. | ΔBP mmHg After 1 hour | ΔBP mmHg After 3 hours | ° Duration hr |
|---|---|---|---|
| 1 | −75 | −80.5 | 7–24 |
| 12 | −30 | −55 | 24< |
| 15 | " | −35 | 7–24 |
| 16 | −55 | −60 | 24< |
| 27 | −130 | −113 | " |
| 44 | −30 | −70 | 7–24 |

TABLE 4-continued

| Derivatives of the Invention Ex. No. | ΔBP mmHg After 1 hour | ΔBP mmHg After 3 hours | Duration hr |
|---|---|---|---|
| 50 | −75 | " | " |
| 55 | −65 | −75 | 24< |
| 61 | −40 | −100 | " |
| A | −45 | −22.0 | <7 |
| B | −27 | −4.5 | <3 |

EXAMPLE 89

Using each trans-form or cis-form of the 1,4-dihydropyridine derivative prepared in Example 1 or 12, the depressor response of the rat was measured in the same manner as Example 87.

The results are shown in the following tables.

TABLE 5

| Derivatives of the Invention Ex. No. | Dose μg/kg i.v. | MaxΔBP mmHg | Peak min | MaxΔHR*1 beats/min | T ½*2 min |
|---|---|---|---|---|---|
| 1 trans | 10 | 35.0 | 2.0 | 28.3 | 32.6 |
|  | 30 | 52.2 | 1.8 | 65.3 | 26.7 |
|  | 100 | 69.0 | 2.0 | 32.5 | 48.5 |
| cis | 10 | 16.0 | 1.2 | 30.0 | 6.3 |
|  | 30 | 40.3 | 1.3 | 80.0 | 11.9 |
|  | 100 | 67.5 | 1.8 | 87.5 | 32.0 |
| 12 trans | 10 | 21.7 | 2.8 | 43.3 | 11.3 |
|  | 30 | 54.8 | 4.1 | 90.0 | 16.0 |
|  | 100 | 72.5 | 4.3 | 80.0 | 37.5 |
| cis | 10 | 12.0 | 3.2 | 23.3 | 14.0 |
|  | 30 | 26.8 | 2.6 | 62.5 | 15.0 |
|  | 100 | 68.5 | 3.8 | 120 | 25.0 |

*1 Heart rates
*2 Half-life

TABLE 6

| Derivatives of the Invention Ex. No. | $ED_{40}$ μg/kg i.v. |
|---|---|
| 1 trans | 15.6 (y = 34 X −0.7 r = 0.797) |
| cis | 29.9 (y = 51.7 X −36.3 r = 0.936) |
| 12 trans | 19.9 (y = 52.2 X −27.8 r = 0.945) |
| cis | 40.8 (y = 54 X −47.0 r = 0.918) |

EXAMPLE 90

Using each trans-form or cis-form of the 1,4-dihydropyridine derivative of Example 2, the time course of the depressor response was observed in the same manner as described in Example 88.

The results are shown in the attached drawing. In the drawing, the open circles indicate the transform derivative, the closed circles indicate the cis-form, and the cross indicates a control experiment wherein a placebo was administered.

In the foregoing Tables, the symbol < means "greater than" and the symbol > means "less than". For example, in Table 1, derivative of Ex. No. 1 (trans), then entry "90<" means that the duration of the blood pressure reducing activity was greater than (longer than) 90 minutes.

When the compounds of formula (II), according to the present invention, and salts thereof, are used as antihypertensive agents for treatment of various hypertensions such as essential hypertension, renal hypertension and malignant hypertension, they are administered orally or non-orally (intermuscular, hypodermic or intravenous administration or in the form of suppositories). The administration doses are changed appropriately according to the body weight and age of the patient, the disease condition, the application method and other factors, but generally, they are administered to adult humans in amounts of 10 to 1,500 mg per day.

The compounds of the present invention are formed into tablets, granules, powders, capsules, injectable solutions, suppositories and the like according to processes customarily employed in the art.

When a solid medicine for oral administration is prepared, an excipient is added to the active ingredient, and adjuvants such as a binder, a disintegrator, a lubricant, a colorant, an odor improver and a taste improver are added. Then, the mixture is formed into tablets, coated tablets, granules, powders and capsules according to customary procedures.

As the excipient, there are used, for example, lactose, corn starch, white sugar, glucose, sorbitol and crystalline cellulose, and as the binder, there are used, for example, polyvinyl alcohol, polyvinyl ether, ethyl celluloe, methyl cellulose, gum arabic, tragacanth gum, gelatin, shellac, hydroxyethyl cellulose, hydroxypropyl cellulose, polyvinyl pyrrolidone, white sugar and sorbital. As the disintegrator, there are used, for example, starch, agar, powdery gelatin, crystalline cellulose, calcium carbonate, sodium hydrogencarbonate, calcium citrate, dextrin, pectin and calcium carboxymethyl cellulose, and as the lubricant, there are used, for example, magnesium stearate, talc, polyethylene glycol, silica and hardened vegetable oils. Colorants which are officially allowed to be incorporated into medicines are used, and as the odor or taste improver, there are used, for example, cacao powder, menthol, aromatic powder, peppermint oil and cinnamon powder. Tablets and granules may be coated with sugar, gelatin or the like.

When a liquid preparation for oral administration is formed, appropriate adjuvants such as an odor or taste improver, a buffering agent and a stabilizer are added to the active ingredient according to need and the mixture is formed into a syrup according to customary procedures.

When an injectable solution is formed, appropriate adjuvants such as a pH-adjusting agent, a buffering agent, a suspending agent, a solubilizing assistant, a stabilizer, an isotonic agent and a preserving agent are added to the active ingredient according to need, and the mixture is formed into hypodermic, intramuscular and intravenous injections according to customary procedures.

As the suspending agent, there are used, for example, methyl cellulose, Polysorbate 80, hydroxyethyl cellulose, gum arabic, tragacanth powder, sodium carboxymethyl cellulose and polyoxyethylene sorbitan monolaurate, and as the solubilizing assistant, there are used, for example, polyoxyethylene-hardened castor oil, Polysorbate 80, nicotinic amide, polyoxyethylene sorbitan monolaurate, macrogol, and cator oil fatty acid ether ester. As the stabilizing agent, there are used, for example, sodium sulfite, sodium metasulfite and diethyl ether, and as the preserving agent, there are used, for example, methyl p-hydroxybenzoate, ethyl p-hydroxybenzoate, sorbic acid, phenol, cresol and chlorocresol.

We claim:

1. A 1,4-dihydropyridine compound having the formula,

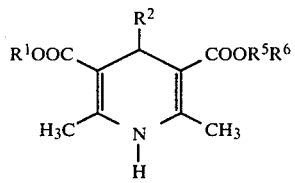

in which
$R^1$ represents a first, saturated or unsaturated, straight chain, branched chain or cyclic hydrocarbon group having a carbon number of 1 to 6, or a derivative of said first hydrocarbon group in which one or more carbon atoms of said first hydrocarbon group are replaced by oxygen atom(s) or sulfur atom(s) or in which one or more hydrogen atoms of said first hydrocarbon group are replaced by phenyl group(s), phenoxy group(s) or phenylthio group(s), $R^2$ represents a substituted phenyl group in which one or more hydrogen atoms of the phenyl group are replaced by nitro group(s), halogen atom(s), alkylthio group(s) or cyano group(s), and $R^5$ is a second, unsaturated, straight chain hydrocarbon group or a derivative of said second hydrocarbon group in which one or more hydrogen atoms of said second hydrocarbon group are replaced by phenyl group(s) or in which one or more hydrogen atoms bonded to the carbon atom at the 1-position of said second hydrocarbon group are replaced by lower alkyl group(s), and $R^6$ is a third, unsaturated hydrocarbon group or a fourth, unsaturated cyclic compound group which is selected from the group consisting of phenyl, naphthyl, furyl, thienyl, pyrrolyl and derivatives of said fourth group in which one or more hydrogen atoms of said fourth group are replaced by cyano group(s), nitro group(s) or methyl group(s), in which an unsaturated carbon atom of $R^5$ is connected to an unsaturated carbon atom of $R^6$ by a single bond and said unsaturated carbon atoms of $R^5$ and $R^6$ are in conjugated relationship to each other.

2. A 1,4-dihydropyridine compound as claimed in claim 1 in which $R^1$ is selected from the group consisting of 2-methoxyethyl, 2-ethylthioethyl, 2-phenoxyethyl, 2-phenylthioethyl, 3-phenyl-2-propenyl, 3-phenyl-2-propynyl and 3-phenyl-1-methyl-2-propenyl, $R^2$ is 3-nitrophenyl, and —$R^5R^6$ is selected from the group consisting of 3-phenyl-2-propenyl, 3-phenyl-1-methyl-2-propenyl and 5-phenyl-2,4-pentadienyl.

3. A 1,4-dihydropyridine compound as claimed in claim 1 in which $R^1$ is methyl, ethyl or propyl, $R^2$ is 3-nitrophenyl, and —$R^5R^6$ is selected from the group consisting of 3-phenyl-1-methyl-2-propenyl, 3-phenyl-1,1-dimethyl-2-propenyl, 3-phenyl-1-ethyl-2-propenyl, 3-phenyl-1-butyl-2-propenyl, 1,3-diphenyl-2-propenyl, 2,3-diphenyl-2-propenyl and 3,3-diphenyl-2-propenyl.

4. A 1,4-dihydropyridine compound as claimed in claim 1 in which $R^1$ is selected from the group consisting of methyl, ethyl, propyl, butyl, propenyl, butenyl, hexadienyl, cyclohexyl, cyclopropylmethyl, 2-methoxyethyl, benzyl and 3-phenyl-2-propenyl, $R^2$ is 3-nitrophenyl, and —$R^5R^6$ is 2,4-hexadienyl.

5. A 1,4-dihydropyridine compound as claimed in claim 1 in which $R^1$ is methyl, $R^2$ is 3-nitrophenyl, and —$R^5R^6$ is selected from the group consisting of 3-(2-naphthyl)-2-propenyl, 3-(1-naphthyl)-2-propenyl, 4-(2-naphthyl)-3-butenyl, 5-(2-naphthyl)-2,4-pentadienyl, 5-(1-naphthyl)-2,4-pentadienyl, 4-(4-cyanophenyl)-3-butenyl, 4-(4-nitrophenyl)-3-butenyl and 4-(4-methylphenyl)-3-butenyl.

6. A 1,4-dihydropyridine compound as claimed in claim 1 in which $R^1$ is methyl, $R^2$ is 3-nitrophenyl, and —$R^5R^6$ is selected from the group consisting of 3-(2-furyl)-2-propenyl, 3-(2-furyl)-1-methyl-2-propenyl, 3-(2-thienyl)-1-methyl-2-propenyl, 4-(3-thienyl)-3-butenyl, 4-(2-thienyl)-3-butenyl and 4-(N-methyl-2-pyrrolyl)-3-butenyl.

7. A 1,4-dihydropyridine compound as claimed in claim 1 in which $R^1$ is methyl, $R^2$ is a substituted phenyl group in which one hydrogen atom is replaced by an alkylthio group, a halogen atom or cyano group, and —$R^5R^6$ is 3-phenyl-2-propenyl group or hexadienyl group.

8. A 1,4-dihydropyridine compound as claimed in claim 1, in which $R^2$ is 3-nitrophenyl, —$R^5R^6$ is 3-phenyl-2-propenyl and $R^1$ is 2-methoxyethyl.

9. A 1,4-dihydropyridine compound as claimed in claim 1, in which $R^2$ is 3-nitrophenyl, $R^1$ is methyl and —$R^1R^6$ is 3-(2-furyl)-2-propenyl.

10. A 1,4-dihydropyridine compound as claimed in claim 1, in $R^2$ is 3-nitrophenyl, $R^1$ is methyl and —$R^5R^6$ is 4-(2-thienyl)-3-butenyl.

11. A 1,4-dihydropyridine compound as claimed in claim 1, in which $R^2$ is 3-nitrophenyl, $R^1$ is methyl and —$R^5R^6$ is 4-$\beta$-naphthyl-3-butenyl.

12. A 1,4-dihydropyridine compound as claimed in claim 1, in which $R^2$ is 3-nitrophenyl, and $R^1$ is methyl and —$R^5R^6$ is 4-(4-cyanophenyl)-3-butenyl.

13. A 1,4-dihydropyridine compound as claimed in claim 1, in which $R^2$ is 3-nitrophenyl, $R^1$ is methyl and —$R^5R^6$ is 4-(p-nitrophenyl)-3-butenyl.

14. A 1,4-dihydropyridine compound as claimed in claim 1, in which $R^2$ is 3-nitrophenyl, $R^1$ is methyl and —$R^5R^6$ is 4-(3-thienyl)-3-butenyl.

15. A 1,4-dihydropyridine compound as claimed in claim 1, in which $R^2$ is 3-nitrophenyl, $R^1$ is methyl and —$R^5R^6$ is 1,3-diphenyl-2-propenyl.

16. A 1,4-dihydropyridine compound as claimed in claim 1, in which $R^2$ is 3-nitrophenyl, $R^1$ is methyl and —$R^5R^6$ is 1-methyl-3-phenyl-2-propenyl.

17. A 1,4-dihydropyridine compound as claimed in claim 1, in which $R^2$ is 3-nitrophenyl, which $R^1$ is methyl and —$R^5R^6$ is 2,4-hexadienyl.

18. A pharmaceutical composition for treating hypertension comprising an effective amount of a compound as claimed in claim 1 in combination with a pharmaceutically acceptable carrier.

19. A method of treating a hypertensive patient which comprises administering to said patient an effective amount of a pharmaceutical composition as claimed in claim 18.

* * * * *

Notice of Adverse Decision in Interference

In Interference No. 102,045, involving Patent No. 4,672,068, T. Kutsuma, H. Ikawa, Y. Sato, ANTIHYPERTENSIVE 1, 4-DIHYDROPYRIDINES HAVING A CONJUGATED ESTER, final judgment adverse to the patentees was rendered Apr. 5, 1990, as to claims 1, 3-7 and 9-19.

(*Official Gazette May 8, 1990*)